(12) United States Patent
Salic

(10) Patent No.: US 8,987,514 B2
(45) Date of Patent: Mar. 24, 2015

(54) COMPOSITIONS AND METHODS FOR LABELING AND IMAGING PHOSPHOLIPIDS

(75) Inventor: Adrian Salic, Cambridge, MA (US)

(73) Assignee: President and Fellows of Harvard College, Cambridge, MA (US)

(*) Notice: Subject to any disclaimer, the term of this patent is extended or adjusted under 35 U.S.C. 154(b) by 721 days.

(21) Appl. No.: 13/147,453

(22) PCT Filed: Feb. 4, 2010

(86) PCT No.: PCT/US2010/023139
§ 371 (c)(1),
(2), (4) Date: Sep. 28, 2011

(87) PCT Pub. No.: WO2010/091142
PCT Pub. Date: Aug. 12, 2010

(65) Prior Publication Data
US 2012/0028290 A1     Feb. 2, 2012

Related U.S. Application Data

(60) Provisional application No. 61/149,813, filed on Feb. 4, 2009.

(51) Int. Cl.
| | | |
|---|---|---|
| *C12Q 1/02* | (2006.01) | |
| *C07C 213/00* | (2006.01) | |
| *C07C 215/00* | (2006.01) | |
| *C07C 217/00* | (2006.01) | |
| *C07C 247/00* | (2006.01) | |
| *A61K 49/00* | (2006.01) | |
| *A61K 47/48* | (2006.01) | |
| *G01N 33/92* | (2006.01) | |
| *G01N 1/30* | (2006.01) | |

(52) U.S. Cl.
CPC ......... *A61K 49/0041* (2013.01); *A61K 47/4813* (2013.01); *G01N 1/30* (2013.01); *G01N 33/92* (2013.01)
USPC .................. 564/293; 552/10; 552/12; 435/29

(58) Field of Classification Search
CPC .... C07C 215/22; C07C 215/24; C07C 24/02; C07C 24/04; C07C 24/06; C07C 24/08; C07C 24/10; C07C 24/12; C07C 24/14; C07C 24/16; C07C 24/18; C07C 24/20; C07C 24/22; C07C 24/24
USPC ........................................ 564/293; 552/10, 12
See application file for complete search history.

(56) References Cited

U.S. PATENT DOCUMENTS

2008/0268468 A1    10/2008    Wong et al.

FOREIGN PATENT DOCUMENTS

| EP | 0 915 086 | 5/1999 |
|---|---|---|
| GB | 839289 | 6/1960 |
| WO | WO-00/45634 | 8/2000 |
| WO | WO 0045634 A1 * | 8/2000 |
| WO | WO-00/71757 | 11/2000 |
| WO | WO-2004/024939 | 3/2004 |
| WO | WO-2006/135233 | 12/2006 |
| WO | WO-2007/022012 | 2/2007 |
| WO | WO-2007/047668 | 4/2007 |
| WO | WO-2007/050811 | 5/2007 |
| WO | WO-2007/104948 | 9/2007 |
| WO | WO-2007/120191 | 10/2007 |
| WO | WO-2007/147482 | 12/2007 |
| WO | WO-2008/029281 | 3/2008 |
| WO | WO-2008/079907 | 7/2008 |
| WO | WO-2009/064696 | 5/2009 |

OTHER PUBLICATIONS

Greenberg et al., "Incorporation of fatty acids containing photosensitive groups into phospholipids of *Escherichia coli*," Proc. Nat. Acad. Sci. USA, 73(1), 86-90, 1976.*
Neef et al., "Selective Fluorescence Labeling of Lipids in Living Cells," Angew. Chem. Int. Ed., 48, 1498-1500, 2009).*
Spector et al., "Membrane lipid composition and cellular function," Journal of Lipid Research, 26, 1015-1035, 1985.*
Baskin et al., "Copper-free click chemistry for dynamic in vivo imaging," PNAS, 104(43):16793-16797 (2007).
Beatty et al., "Fluorescence Visualization of Newly Synthesized Proteins in Mammalian Cells," Angew. Chem. Int. Ed., 45:7364-7367 (2006).
Bieber et al., "The incorporation of dimethylaminoethanol and dimethylaminoisopropyl alcohol into *Phormia regina* phospholipids," J. Lipid. Res., 4:397-401 (1963).
Bridges et al., "The Incorporation of Analogues of Choline Into the Phospholipids of the Larva of the Housefly, *Musca domestica*," J. Insect. Physiol., 16:579-593 (1970).
Codelli et al., "Second-Generation Difluorinated Cyclooctynes for Copper-Free Click Chemistry," J. Am. Chem. Soc., 130:11486-11493 (2008).
Dowhan, W., "Molecular Basis for Membrane Phospholipid Diversity: Why Are There So Many Lipids?," Annual Review of Biochemistry, 66:199-232 (1997).
Hodgson et al., "The Nutrition of Choline, Carnitine, and Related Compounds in the Blowfly, *Phormia regina* Meigen," J. Insect. Physiol., 19:1005-1008 (1964).
Ikramov et al., Zhurnal Prikladnoi Khimii, 65(2):465-467 (1992).
Jao et al., "Exploring RNA transcription and turnover in vivo by using click chemistry," PNAS, 105(41):15779-15784 (2008).

(Continued)

*Primary Examiner* — Paul A Zucker
*Assistant Examiner* — Mark Luderer
(74) *Attorney, Agent, or Firm* — Foley Hoag LLP

(57) ABSTRACT

The present invention provides a method to label phospholipids in vivo based on the metabolic incorporation of an alkynyl- or azido-labeled metabolic precursor into phospholipids. The resulting phospholipids have alkynyl or azido moieties, which, upon reaction with a labeled azide or alkyne, respectively, form labeled compounds that can be visualized using optical or electron microscopy with high sensitivity and spatial resolution in cells or tissue. The present method provides a valuable tool for imaging phospholipid synthesis, turnover and subcellular localization in cultured cells as well as in animals.

17 Claims, 11 Drawing Sheets

(56) References Cited

OTHER PUBLICATIONS

Jao et al., "Metabolic labeling and direct imaging of choline phospholipids in vivo," PNAS, 106(36):15332-15337 (2009).
Kiick et al., "Incorporation of azides into recombinant proteins for chemoselective modification by the Staudinger ligation," PNAS, 99(1):19-24 (2002).
Kwee et al., "Cancer Imaging With Fluorine-18-Labeled Choline Derivatives," Seminars in Nuclear Medicine, 37(6):420-428 (2007).
Lebbin et al., "Affinity-Labelling of the Muscarinic Receptor of the Guinea-Pig Ileum," NaunynSchmiedeberg's Archives of Pharmacology, 289(3):237-249 (1975).
Macara, I., "Elevated Phosphocholine Concentration in ras-Transformed NIH 3T3 Cells Arises from Increased Choline Kinase Activity, Not from Phosphatidylcholine Breakdown," Molecular and Cellular Biology, 9(1):325-328 (1989).
Montecucco et al., "Labelling of the Subunits of the Mitochondrial Adenosine Triphosphatase Complex in Contact with the Lipid Bilayer," Biochemical Society Transactions, 7(5):954-955 (1979).
Nagan et al., "Plasmalogens: biosynthesis and functions," Progress in Lipid Research, 40:199-229 (2001).
Panchuk-Voloshina et al., "Alexa Dyes, a Series of New Fluorescent Dyes that Yield Exceptionally Bright, Photostable Conjugates," The Journal of Histochemistry & Cytochemistry, 47(9):1179-1188 (1999).
Pasternak et al., "Turnover of Mammalian Phospholipids," Biochem. J., 119:481-488 (1970).
Petcoff et al., "Lipid levels in sperm, eggs, and during fertilization in *Xenopus laevis*," Journal of Lipid Research, 49:2365-2378 (2008).
Ponpipom et al., "Synthesis of Azide and Amide Analogs of Platelet-Activating Factor and Related Derivatives," Chemistry and Physics of Lipids, 35(1):29-37 (1984).
Ragunathan et al., "Formation of gel and fibrous microstructures by 1-alkyne amphiphiles bearing L-serine headgroup in organic solvents," Chemistry and Physics of Lipids, 77:13-23 (1995).
Rostovtsev et al., "A Stepwise Huisgen Cycloaddition Process: Copper(I)-Catalyzed Regioselective "Ligation" of Azides and Terminal Alkynes," Angew. Chem. Int. Ed. 41(14):2596-2599 (2002).
Salic et al., "A chemical method for fast and sensitive detection of DNA synthesis in vivo," PNAS, 105(7):2415-2420 (2008).
Saxon et al., "Cell Surface Engineering by a Modified Staudinger Reaction," Science, 287(5460):2007-2010 (2000).
Sletten et al., "A Hydrophilic Azacyclooctyne for Cu-Free Click Chemistry," Organic Letters, 10(14):3097-3099 (2008).
Tornøe et al., "Peptidotriazoles on Solid Phase: [1,2,3]-Triazoles by Regiospecific Copper (I)-Catalyzed 1,3-Dipolar Cycloadditions of Terminal Alkynes to Azides," J. Org. Chem., 67(9):3057-3064 (2002).
Tumaney et al., "Synthesis of azidophospholipids and labeling of lysophosphatidylcholine acyltransferase from developing soybean cotyledons," Biochimica et Biophysica Acta, 1439(1):47-56 (1999).
Vance et al., "Phospholipid biosynthesis in mammalian cells," Biochem. Cell Biol., 82:113-128 (2004).
Villa et al., "Choline and phosphatidylcholine fluorescent derivatives localization in carcinoma cells studied by laser scanning confocal fluorescence microscopy," European Journal of Cancer, 41(10):1453-1459 (2005).
Vocadlo et al., "A chemical approach for identying O-GlcNAc-modified proteins in cells," PNAS, 100(16):9116-9121 (2003).
Weiss et al., "The Enzymatic Formation of Lecithin from Cytidine Diphosphate Choline and d-1,2-Diglyceride," J. Biol. Chem., 231:53-64 (1958).
International Search Report dated Jul. 22, 2010, from PCT/US2010/023139.

\* cited by examiner

COMPOSITIONS AND METHODS FOR LABELING AND IMAGING PHOSPHOLIPIDS

RELATED APPLICATION

This application is the U.S. National Stage of International Patent Application No. PCT/US2010/023139, filed Feb. 4, 2010, which claims the benefit of priority to U.S. Provisional Patent Application Ser. No. 61/149,813, filed Feb. 4, 2009.

BACKGROUND

Phospholipids are the major lipid components of all cellular membranes. There are two classes of phospholipids: those that have a glycerol backbone and those that contain sphingosine. Both classes are present in the biological membranes. Sphingomyelin is the major sphingosine-containing phospholipid. Its general structure consists of a fatty acid attached to sphingosine by an amide linkage. Phospholipids that contain a glycerol backbone are called phosphoglycerides (or glycerophospholipids); these constitute the most abundant class of phospholipid found in nature. The most abundant types of naturally occurring phosphoglyceride are phosphatidylcholine (lecithin), phosphatidylethanolamine, phosphatidylserine, phosphatidylinositol, phosphatidylglycerol, and cardiolipin (Vance, J. E., and Vance, D. E. (2004) Phospholipid biosynthesis in mammalian cells. *Biochem Cell Biol.*, 82, 113-128) The structural diversity within each type of phosphoglyceride is due to the variability of the chain length and degree of saturation of the fatty acid ester groups.

Choline-containing phospholipids have important structural roles in membranes and also play critical roles in cell signaling, either as signaling molecules in their own right or as precursors, through enzymatic hydrolysis, of lipid secondary messengers. Choline is a vitamin, an essential nutrient for most animal cells. Choline enters the cell through specific membrane transporters, and is phosphorylated by choline kinase, after which choline is usually activated as cytidine diphosphate (CDP)-choline (Weiss, S. B., et al. (1958) The enzymatic formation of lecithin from cytidine diphosphate choline and D-1,2-diglyceride. *J Biol Chem,* 231, 53-64). In the most common pathway for the biosynthesis of choline phospholipids, choline is transferred from CDP-choline to the head group of various phospholipid species, a reaction that takes place in the endoplasmic reticulum. Choline-containing phospholipids are chemically diverse, including phosphatidylcholine, sphingomyelin and ether phospholipids with a choline head group. Phosphatidylcholine is the most abundant phospholipid in most eukaryotic cells, comprising almost 50% of the phospholipid pool. Sphingomyelin is an important component of axonal myelin sheaths, making up 10% of the phospholipids in brain. Choline-containing ether lipids are less abundant, except in white blood cells, in which they reach half the level of phosphatidylcholine (Nagan, N., and Zoeller, R A. (2001) Plasmalogens: biosynthesis and functions, *Prog Lipid Res.,* 40, 199-229), and are precursors of the platelet-activating factor (PAP), a choline phospholipid with potent inflammatory activity.

The cell biology of phospholipids is not well-understood. Progress in understanding the cell biology of choline phospholipids would be greatly aided by having the ability to metabolically label them followed by their high-resolution microscopic imaging in cells.

SUMMARY

The present invention relates in part to compositions and methods for metabolically labeling phospholipids, and for visualizing the labeled phospholipids in cultured cells and in animals. In certain embodiments, the method comprises forming an alkynyl-functional analog of a metabolic phospholipid precursor by reacting the precursor with a compound comprising an alkyne moiety, thereby forming an analog which bears an alkynyl functional group. In certain embodiments, the method comprises forming an azido-functional analog of a metabolic phospholipid precursor by reacting the precursor with a compound comprising an azido moiety, thereby forming an analog which bears an azido functional group. The alkynyl-precursor analog or azido-precursor analog then is contacted with living cells, e.g., cultured cells or cells in a living animal, under conditions wherein the analog becomes incorporated into the endogenous phospholipids in the cells through cellular metabolic processes. The resulting phospholipids containing the alkynyl or azido moiety then can be detected and visualized in the cells by contacting the cells with an azide or alkyne compound, respectively, bearing a detectable label under conditions sufficient to allow the azide moiety to react with the alkynyl or azido moiety, to form a 1,2,3-triazole, and visualizing the resulting labeled phospholipid compounds via optical or electron microscopy.

In certain embodiments, a phospholipid head group precursor is reacted with a compound containing an alkynyl group. Alkynyl-containing compounds useful in the present invention include any compound that (1) has a reactive alkynyl moiety, (2) can react with the phospholipid head group precursor to form an alkynyl analog (e.g., has a leaving group), and (3) does not prevent the resulting analog from being efficiently incorporated into phospholipids; that is, allows the analog to participate in metabolic reactions in a manner similar to the precursor itself. In certain embodiments, the alkynyl-containing compound is a linear alkyl-alkyne having two to five carbon atoms, or a cyclic alkynyl compound, which may have up to about eight carbon atoms, and a leaving group. In certain embodiments, the alkynyl-containing compound is an alkynyl halide (e.g., prop argyl-bromide).

In other embodiments, a phospholipid head group precursor is reacted with a compound containing an azido group. Azido-containing compounds useful in the present invention include any compound that (1) has a reactive azido moiety, (2) can react with the phospholipid head group precursor to form an azido analog, and (3) does not prevent the resulting analog from being efficiently incorporated into phospholipids; that is, allows the analog to participate in metabolic reactions in a manner similar to the precursor itself. In certain embodiments, the azido-containing compound is a linear alkyl-azide having one to five carbon atoms, and a leaving group. In certain embodiments, the azido-containing compound is an azidoalkylhalide (e.g., azidoethylbromide).

The invention further comprises novel alkynyl derivatives of head group precursors, and phospholipid molecules containing these derivatives. Head group precursors include, for example, choline, homocholine, inositol, serine and ethanolamine.

The invention further comprises novel azide derivatives of head group precursors, and phospholipid molecules containing these derivatives.

The invention further comprises assays and methods for determining the presence of disorders relating to phospholipid biosynthesis, utilization or distribution, or characterized by improper phospholipid localization, in living cells or tissue, such as certain cancers or neurological conditions. The invention further comprises methods for determining the whether a test compound affects or inhibits phospholipid biosynthesis, utilization or distribution in living cells or tissue.

Additional aspects, embodiments, and advantages of the invention are discussed below in detail.

BRIEF DESCRIPTION OF THE FIGURES

FIG. 4A shows co-localization of the propargyl choline stain with subcellular marker in cultured cells that were transfected with plasmids encoding red fluorescent protein fusions that mark various organelles, then labeled with 100 microM propargyl choline overnight; the propargyl choline label was detected with fluorescein-azide. These images show that choline co-localizes with markers for the plasma membrane, the Golgi, mitochondria and endoplasmic reticulum; the white arrows point to subcellular structures that stain for both propargyl choline and the red fluorescent marker. FIG. 4B shows that propargyl choline-labeled phospholipids localize to the outer leaflet of the plasma membrane.

DETAILED DESCRIPTION

Figure 1A:
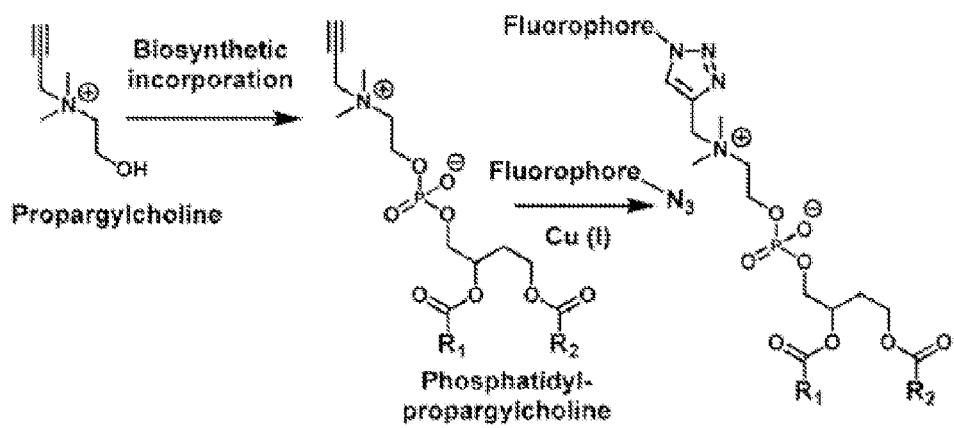
FIG. 1A is a schematic of a preferred embodiment of the invention in which propargyl-choline is incorporated into a phospholipid moiety to form phosphatidyl-propargylcholine, and further reaction of the terminal alkynyl group with a fluorescent azide.

Phospholipids are the fundamental building blocks of cellular membranes and form the major part of surfactant, the film that occupies the air/liquid interfaces in the lung. These molecules consist of a polar or charged head group and a pair of nonpolar fatty acid tails, connected via a glycerol linkage.

The structure of the most common class of phospholipids, phosphoglycerides, is based on glycerol, a three-carbon alcohol with the formula $CH_2OH$—$CHOH$—$CH_2OH$. Two fatty acid chains, each typically having an even number of carbon atoms between 14 and 20, attach (via a dual esterification) to the first and second carbons of the glycerol molecule, denoted as the sn1 and sn2 positions, respectively. The third hydroxyl group of glycerol, at position sn3, reacts with phosphoric acid to form phosphatidate (or phosphatidic acid). Phospholipids are produced by further reaction of the phosphate group in phosphatidate with an alcohol called a "head group." Common phospholipids, widely distributed in nature, contain as head groups serine, ethanolamine, choline, glycerol, and inositol, or derivatives of these, e.g., homocholine. In addition to naturally occurring head group compounds, the invention includes non-naturally-occurring derivatives and stereoisomers, provided that these derivatives and stereoisomers can be metabolized in living cells to form phospholipids.

Fatty acids are carboxylic acids having an unbranched aliphatic tail (chain), which is either saturated or unsaturated. Carboxylic acids as short as butyric acid (4 carbon atoms) are considered to be fatty acids, whereas fatty acids derived from natural fats and oils may be assumed to have at least 8 carbon atoms, e.g., caprylic acid (octanoic acid). Most of the natural fatty acids have an even number of carbon atoms, because their biosynthesis involves acetyl-CoA, a coenzyme carrying a two-carbon-atom group. Fatty acids are aliphatic monocarboxylic acids, derived from, or contained in esterified form in an animal or vegetable fat, oil or wax. Natural fatty acids commonly have a chain of 4 to 28 carbons (usually unbranched and even numbered), which may be saturated or unsaturated. A typical phospholipid arrangement is the presence of a saturated fatty acid, such as palmitic or stearic acid, at the sn1 position, and an unsaturated or polyunsaturated fatty acid, such as oleic or arachodonic acid, at sn2. However, other fatty acids may be present. Eukaryotic cell membranes contain more than a thousand different phospholipid species as a result of various combinations of acyl chains and a variety of polar head groups (Dowhan, (1997) Molecular basis for membrane phospholipid diversity: why are there so many lipids? *Ann Rev. Biochem*, 66, 199-239).

Another class of phospholipids is the sphingolipids. A sphingolipid molecule has the phosphatidyl-based head group structure described above, but (in contrast to a common phospholipid molecule) contains a single fatty acid and a long-chain alcohol as its hydrophobic components. Additionally, the backbone of the sphingolipid is sphingosine, an amino alcohol (rather than glycerol). Sphingolipids occur primarily in nervous tissue, are thought to form cholesterol-rich domains within lipid bilayer membranes that may be important to the functions of some membrane proteins.

The present invention provides methods and compositions for the direct imaging or visualization of phospholipid biosynthesis in cells and tissue. The method comprises forming an alkynyl derivative of a metabolic precursor of the phospholipid head group by reacting the precursor with an alkyne moiety, thereby forming an analog which bears an alkynyl functional group. The head group may be any head group that occurs in eukaryotic cells, including serine, ethanolamine, choline, glycerol, and inositol, or derivatives of these, e.g., homocholine. In a currently preferred embodiment, the head group is choline, homocholine, inositol, serine or ethanolamine.

Alkynyl compounds useful in the present method include any compound that (i) has a reactive alkynyl moiety, (ii) can react with the phospholipid head group precursor to form an alkynyl-analog, and (iii) does not prevent the resulting analog from being efficiently incorporated into phospholipids; that is, allows the analog to participate in metabolic reactions in a manner similar to the precursor itself. In certain embodiments, the alkynyl-containing compound is a linear alkyl-alkyne having two to five carbon atoms, and a leaving group. In certain embodiments, the alkynyl compound is an alkynyl-halide (e.g. propargylbromide). Cyclic alkynyl compounds, which may have up to about eight carbon atoms, also may be used, such as, for example, the cyclooctynes described in Codelli et al. (Codelli et al., (2008) Second-Generation difluorinated cyclooctanes for copper-free click chemistry. *J Am Chem Soc*, 130, 11486-11493) and Sletten and Bertozzi (Stetten and Bertozzi, (2008) A hydrophilic azacyclooctane for Cu-free click chemistry, *Org. Letts*, 10(14), 3097-3099).

Azido-containing compounds useful in the present invention include any compound that (1) has a reactive azido moiety, (2) can react with the phospholipid head group precursor to form an azido analog, and (3) does not prevent the resulting analog from being efficiently incorporated into phospholipids; that is, allows the analog to participate in metabolic reactions in a manner similar to the precursor itself. In certain embodiments, the azido-containing compound is a linear alkyl-azide having between one to five carbon atoms, and a leaving group. In certain embodiments, the azido-containing compound is an azidoalkylhalide (e.g. azidoethylbromide).

The step of reacting the alkynyl compound, or azido compound, with the head group of a phospholipid to form the alkynyl-precursor analog, or the azido-precursor analog, may be carried out by any chemical reaction that results in covalent attachment of the alkynyl compound, or azido compound, to the head group such that the head group retains a free hydroxyl group that is available to react with the phosphate group on the phosphatidate molecule. Where the head group contains more than one reactive site, some or all of these sites may be substituted with an alkynyl or azido moieties. For example, choline contains three methyl groups, any or all of which may be substituted with an alkynyl compound or an azido compound (see FIGS. 7 and 8). In certain embodiments, wherein the alkynyl compound is a linear alkyl, the alkynyl group must be in the terminal position. In other embodiments, wherein a cyclic alkyne is used, the alkyne group may be internal, i.e., part of the ring structure.

The alkynyl- or azido-precursor analog can then be contacted with living cells, e.g., cultured cells or cells in a living animal, where the analog reacts with endogenous phosphatidate molecules in the cells and becomes incorporated into phospholipids through cellular metabolic processes. The resulting phospholipids containing the alkynyl or azido moiety then can be detected and visualized in the cells by contacting the cells with an azide or alkyne compound, respectively, bearing a detectable label under conditions sufficient to allow the azide moiety to react with the alkynyl group, and visualizing the resulting labeled phospholipid compounds, such as via optical or electron microscopy.

The detectable label may be any optically or electronically detectable material or compound that contains or can be modified to include azide or alkyne functional groups. Azide compounds bearing detectable labels which can be used in the present method include azide derivatives of fluorescein, carboxytetramethylrhodamine (TMR), biotin or fluorescent dyes such as Alexa dyes (e.g. Alexa 598). Alexa dyes are described, for example by Panchuk-Voloshina et al. (Panchuk-Voloshina et al., (1999) Alexa dyes, a series of new fluorescent dyes that yield exceptionally bright, photostable conjugates. *J. Histochem & Cytochem.*, 47(9), 1179-1188). Methods of forming azide derivatives of many optical detection agents are known. For example, methods for forming azide derivatives of fluorescein, TMR and Alexa568 are described by Salic and Mitchison (Salic, A., and Mitchison, T J. (2008) A chemical method for fast and sensitive detection of DNA synthesis in vivo. *Proc Natl Acad Sci, USA* 105, 2415-2420), the entirety of which is incorporated herein by reference. See, also, International Patent Application Nos. PCT/US2006/042287 and PCT/US2006/041885, both of which are hereby incorporated by reference in their entireties.

The step of reacting an alkyne with an azide can be carried out by any appropriate method. Such methods include copper-catalyzed cycloaddition reactions for ligating azides and terminal alkynes described by Rostovtsev et al. (Rostovtsev, V. V., et al. (2002) A stepwise huisgen cycloaddition process: copper(I)-catalyzed regioselective "ligation" of azides and terminal alkynes. *Angew Chem Int Ed Eng.*, 41, 2596-2599) and Tornoe (Tornoe, C. W., et al. (2002) Peptidotriazoles on solid phase: [1,2,3]-triazoles by regiospecific copper(i)-catalyzed 1,3-dipolar cycloadditions of terminal alkynes to azides. *J Org Chem*, 67, 3057-306), (these reactions sometimes are referred to as "click chemistry"). The presence of copper is incompatible with living systems, however. Copper-free azide-alkyne cycloaddition reactions such as those described by Codelli (Codelli et al., (2008) Second-Generation difluorinated cyclooctanes for copper-free click chemistry. *J Am Chem Soc*, 130, 11486-11493) and Sletten and Bertozzi (Stetten and Bertozzi, (2008) A hydrophilic azacyclooctane for Cu-free click chemistry, *Org. Letts*, 10(14), 3097-3099), the entirety of both references are incorporated here in by reference, are preferred for imaging in living cells or tissues. These and other azide-alkyne cycloaddition reactions are described in detail on the "clickchemicals.com" website and the references disclosed therein.

Figure 7:
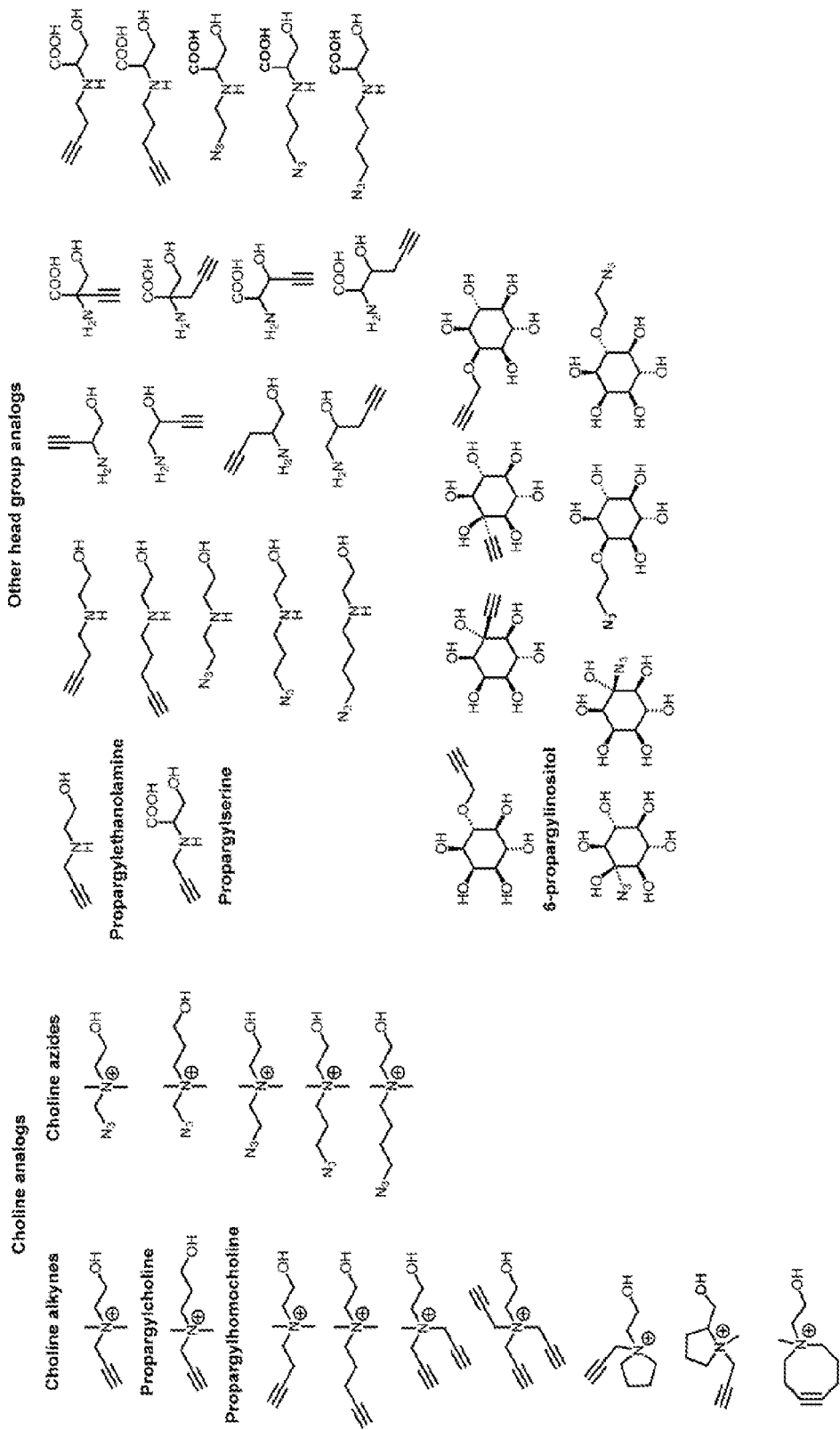
FIG. 7 depicts a table of representative, non-limiting examples of alkynyl and azide derivatives.
Figure 8:
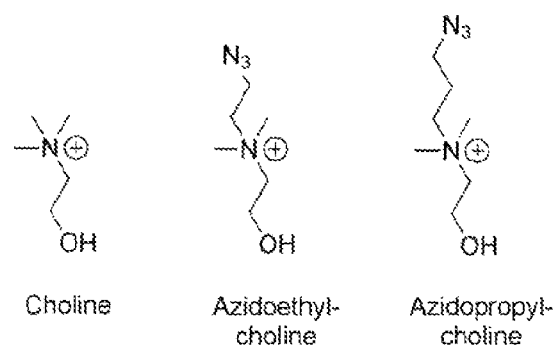
FIG. 8 depicts the structure of two choline analogs bearing azide groups, azidoethyl- and azidopropyl-choline, which are efficiently incorporated into phospholipids in vivo.

The invention further comprises alkynyl derivatives of head group precursors, and phospholipid molecules containing these derivatives. Compounds of the present invention include, for example, alkynyl derivatives of choline, homocholine, inositol, serine and ethanolamine. In certain embodiments, alkynyl compounds used to form the derivatives include linear alkyl-alkynes having between two and five carbon atoms and having a terminal alkynyl group, or cyclic alkynes having up to about eight carbon atoms. The invention further comprises novel azide derivatives of head group precursors, and phospholipid molecules containing these derivatives. Representative, non-limiting examples of the novel alkynyl and azide derivatives are shown in FIGS. 7 and 8.

In certain embodiments of the present invention, propargyl-choline, in which one methyl of the choline molecule is replaced by a three-carbon propargyl group, was synthesized, and its incorporation into cultured mammalian cells in place of choline as a phospholipid building block was tested. Propargyl-choline was synthesized as described in Example 1, and NIH-3T3 cells were incubated with varying concentrations (between 10 microM and 5 milliM) of propargyl choline for 24 hours to permit uptake of the propargyl choline and incorporation into phospholipids by the cells. The cells then were fixed and stained with Alexa568-azide to form the detectable phospholipid. (See FIG. 1A).

Figure 1B:
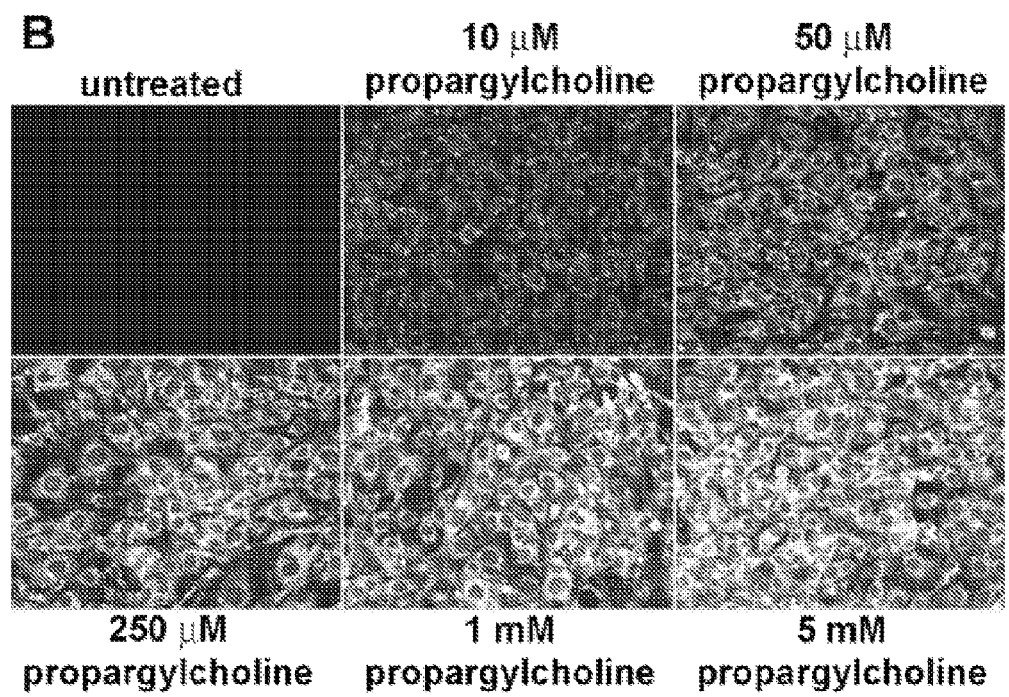
FIG. 1B is a series of images showing the incorporation of varying concentrations of propargyl-choline phospholipids into NIH-3T3 cells.
Figure 1C:
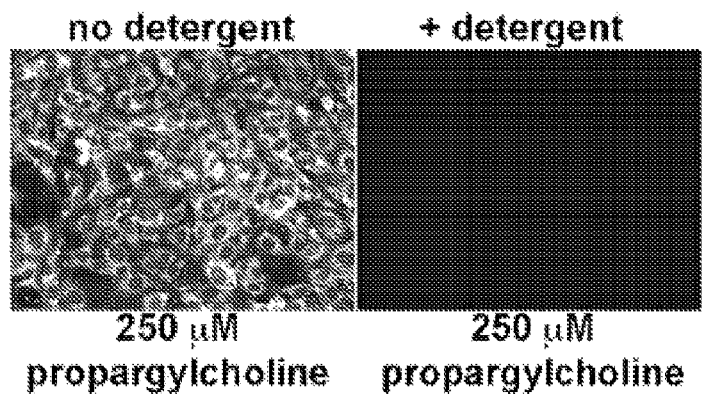
FIG. 1C shows that the intensity of the stain is greatly decreased if cells are permeabilized with detergent before fixation.
Figure 1D:
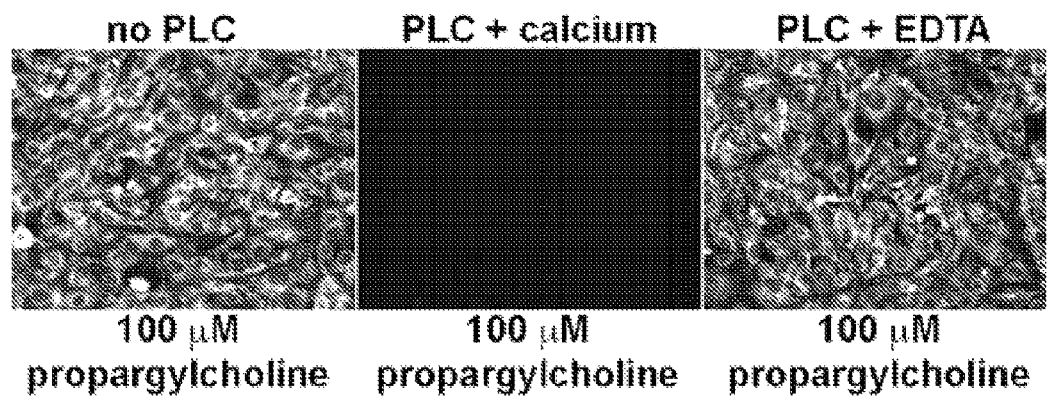
FIG. 1D is a series of images showing that treatment of fixed cells with PLC strongly decreases staining

It was found that cells which were incubated with the propargyl-choline analog overnight evidenced strong staining proportional in intensity to the propargyl-choline analog concentrations, as shown in FIG. 1B. As shown in FIG. 1B, cells labeled overnight with varying concentrations of propargyl choline, then fixed and stained with Alexa568-azide, evidence an increase in staining intensity commensurate with the increasing concentration of propargyl choline. The absence of propargyl choline results in low staining background.

The results of two experiments shown in FIG. 1 support the idea that propargyl-choline is incorporated into phospholipids. First, as shown in FIG. 1C, the propargyl-choline stain is very sensitive to detergents, consistent with the fact that propargyl-choline-labeled phospholipids are not covalently attached to the fixed cells and can be solubilized by detergent. Second, incubation of fixed, propargyl-choline labeled cells with phospholipase C (PLC, which hydrolyzes choline head groups) abolishes the propargyl choline stain (FIG. 1D).

Figure 1E:
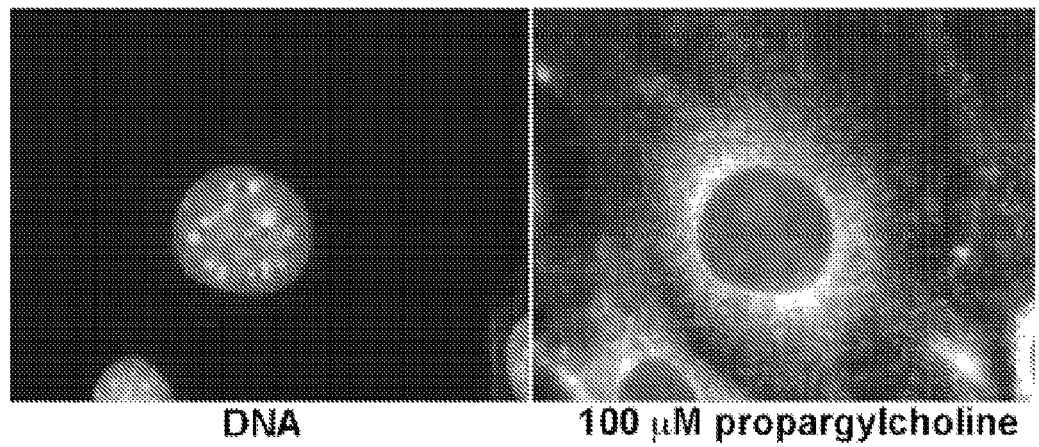
FIG. 1E shows fluorescence micrographs of cells labeled with propargyl choline overnight and then stained with Alexa568-azide and Hoechst (DNA).

FIG. 1E shows higher magnification fluorescence micrograph of cells labeled with propargyl choline overnight and then stained with Alexa568-azide as described above, and Hoechst (DNA). FIG. 1E shows that the propargyl-choline stain localizes to a large number of intracellular structures, including ones that are vesicular, tubular and reticular in shape. The plasma membrane labels strongly, although the signal is significantly smaller than that of intracellular structures. The stain is excluded from the nucleus. Propargyl-choline phospholipid staining of cells was very intense and mostly uniform across the population, with only small cell-to-cell differences.

Figure 4:
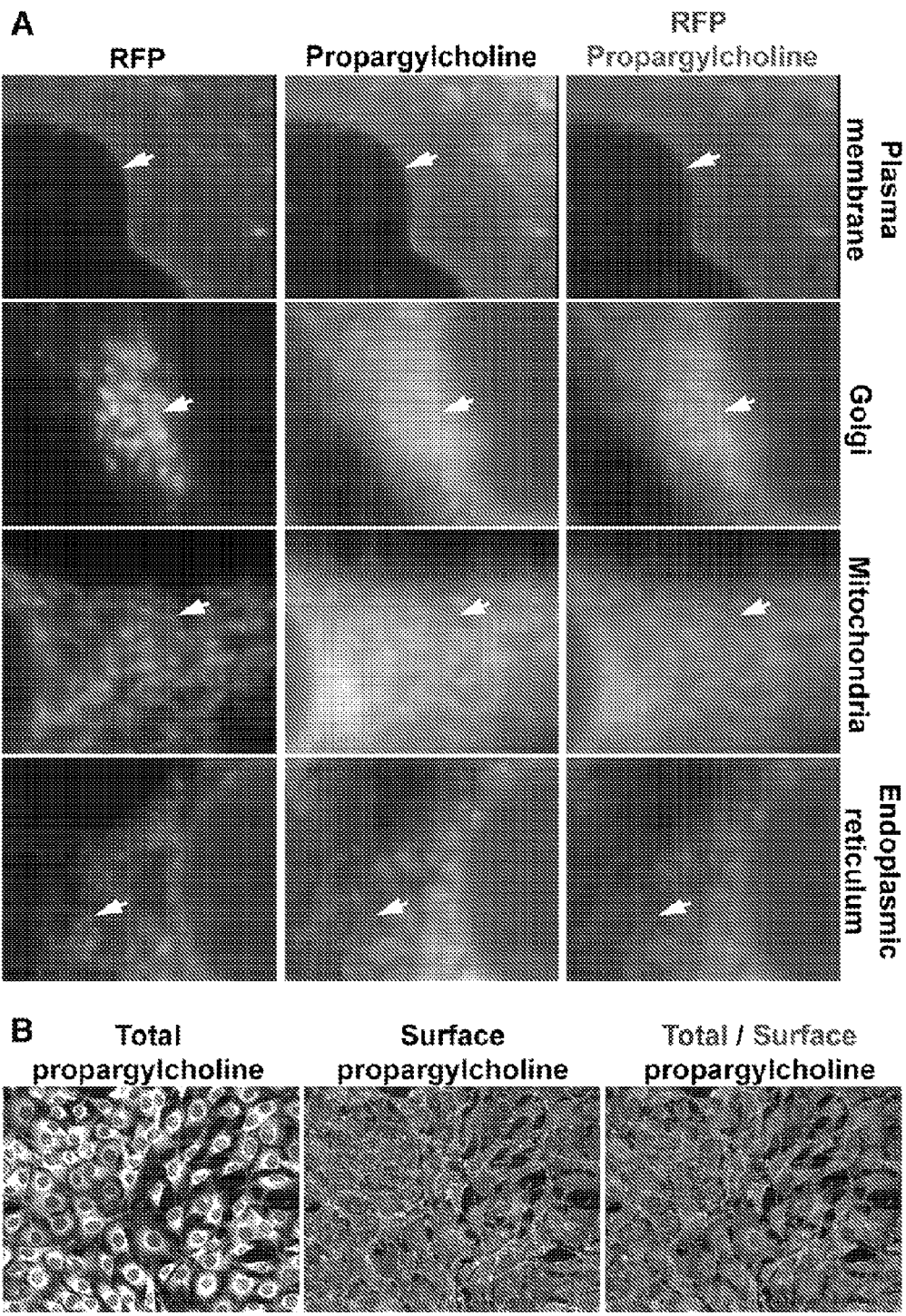
FIG. 4 is a series of images showing the subcellular distribution of propargyl choline-labeled phospholipids.

Other fluorescent azides (such as fluorescein-azide) also stain the propargyl-choline labeled cells with high efficiency (see FIG. 4). All cultured cells were grown in complete media, which contains 30 microM of choline; demonstrating that propargyl-choline can effectively compete with choline in cells for utilization in phospholipid biosynthesis.

Figure 2:
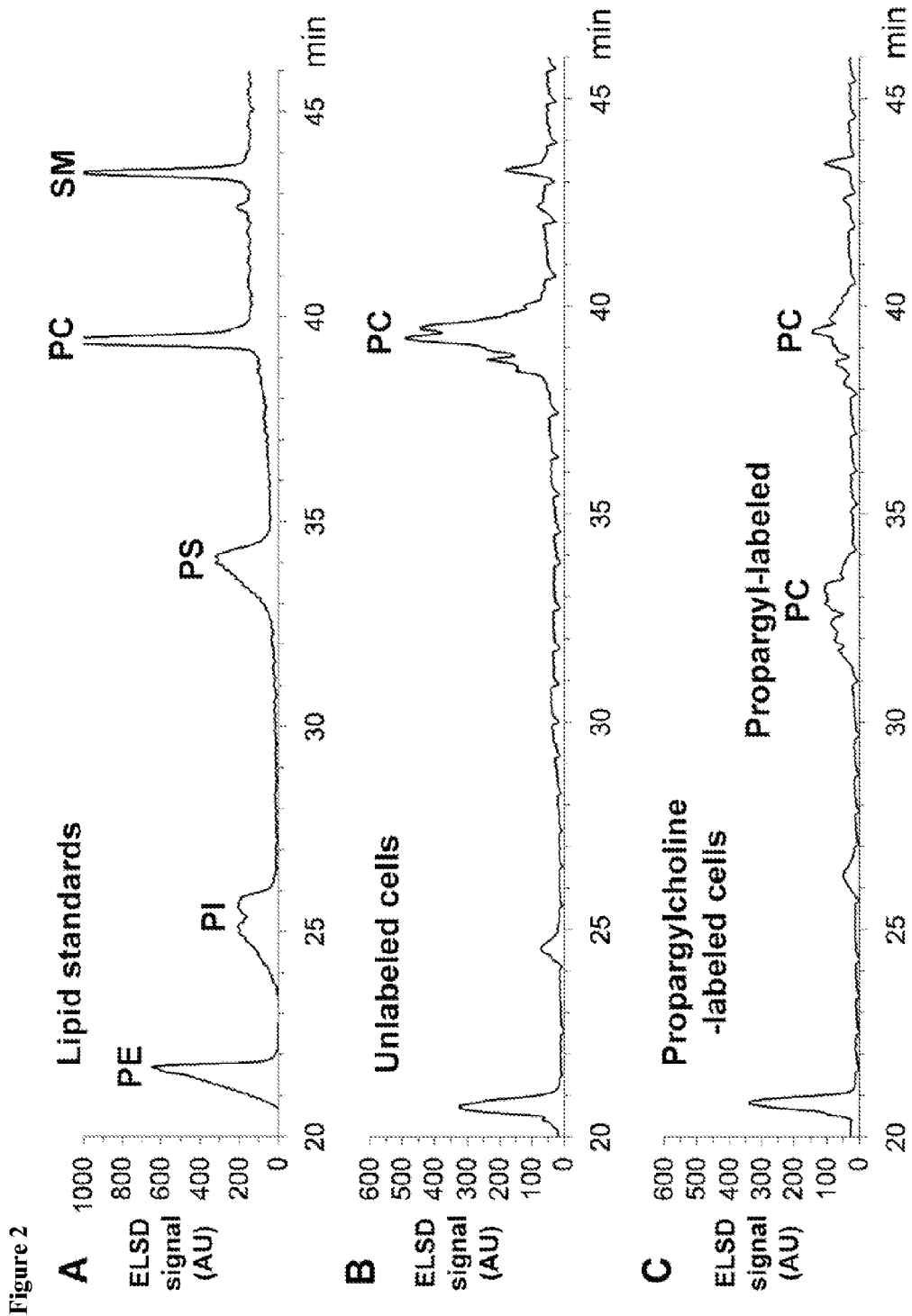
FIG. 2A shows the separation by HPLC of a mix of phospholipid standards: phosphatidylethanolamine (PE), phosphatidylinositol (PI), phosphatidylserine (PS), phosphatidylcholine (PC), and sphingomyelin (SM)
FIG. 2B shows the HPLC results for total lipids from unlabeled cells.
FIG. 2C shows the HPLC results for equal amounts of total lipids from cells labeled with propargyl choline.

The incorporation of propargyl choline into cellular phospholipids was further verified by lipid analysis. In this experiment, NIH-3T3 cells were incubated with or without 500 microM of propargyl choline overnight, followed by isolation of total lipids and their separation by HPLC on a normal phase column. The results, shown in FIG. 2, show that lipids from propargyl choline-labeled cells show a prominent HPLC peak not found in control cells, while also containing less phosphatidylcholine than the controls (compare panels C and B in FIG. 2). To determine which lipid peaks in the chromatograms in FIG. 2 contain choline and propargyl choline, the HPLC-fractionated lipids were subjected to phospholipase D (PLD) treatment (which hydrolyzes choline head groups to choline), followed by LC/MS detection of choline and propargyl choline. This analysis showed that the additional peak seen in propargyl choline-labeled lipid samples contains propargyl choline but not choline, that the phosphatidylcholine peak contains choline but not propargyl choline, and that choline and propargyl choline were not released by PLD treatment of any of the other peaks. The intensity of the additional lipid peak from propargyl choline-labeled cells closely matches the decrease in intensity of the phosphatidylcholine peak, indicating that the new peak represents phosphatidyl-propargylcholine.

The fraction of choline that is substituted by propargyl choline in 293T cells labeled for 24 hours with either 250 microM or 500 microM propargyl choline in normal media (which contains 30 microM choline) was measured. Total lipids extracted from these cells were treated with PLD followed by quantitative LC/MS to measure the molar ratio between the choline and propargyl choline head groups released by PLD hydrolysis. At 250 microM propargyl choline in the media, 36% of choline head groups are replaced with propargyl choline, while at 500 microM propargyl choline, the degree of substitution reaches 86%. This high level of propargyl choline incorporation is consistent with the strong signal observed by microscopy and confirms that propargyl choline is efficiently utilized by cells in place of choline.

Figure 3:
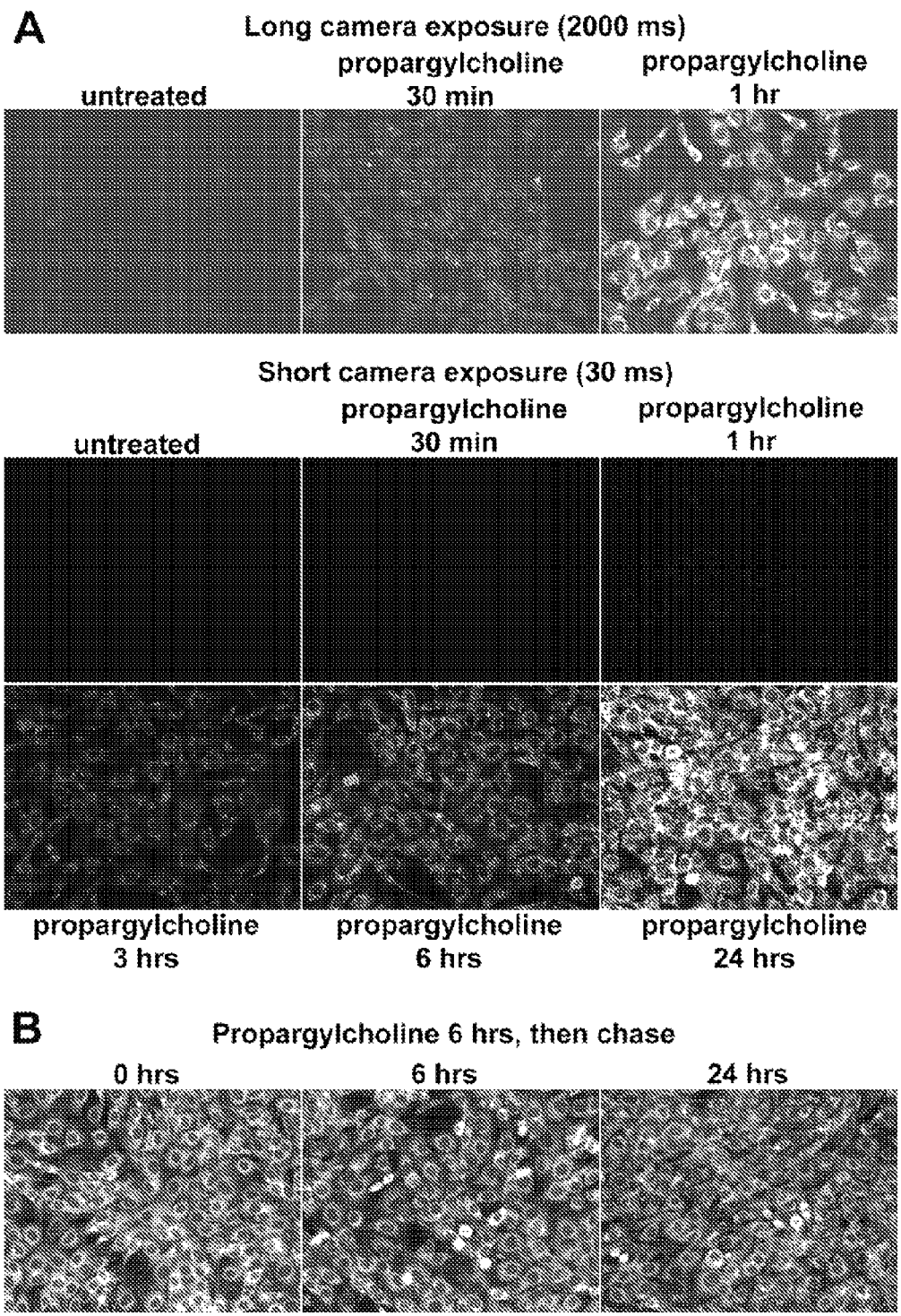
FIG. 3A is a series of images showing the time course of propargyl choline uptake and incorporation into cellular phospholipids in cells labeled with 1 mM of propargyl choline for varying amounts of time, and then stained with Alexa568-azide. The stain was photographed with a long exposure time (2 s, top 3 panels) or a short exposure time (30 ms, bottom 6 panels).
FIG. 3B is a series of images showing the stability of propargyl choline-labeled phospholipids in cells labeled with 1 mM propargyl choline for 6 hrs and then chased with normal media for different amounts of time.

FIG. 3A shows the results of measurements made to determine the kinetics of incorporation of propargyl choline into cells, as well as phospholipid turnover in cells. As shown in FIG. 3A, the intensity of the propargyl choline stain increases gradually with labeling time, reaching very high levels after 24 hours. Strong propargyl choline labeling is visible after 3-6 hours. At longer exposure times, significant propargyl choline staining can be detected even after labeling for only 30 minutes. Propargyl choline thus quickly starts being incorporated into phospholipids and shows sustained incorporation during prolonged cell labeling.

The stability of propargyl choline-labeled phospholipids was determined by pulse-chase. Cells labeled with 1 mM propargyl choline for 6 hours were washed to remove unincorporated propargyl choline and were chased and fixed at different times, followed by azide staining. As shown in FIG. 3B, the intensity of the propargyl choline stain does not appreciably decrease after 24 hours, indicating that propargyl choline-labeled phospholipids are stable. This result is consistent with the measured half-life of mammalian phospholipids labeled with radioactive choline (Pasternak, C. A., and Friedrichs, B. (1970) Turnover of mammalian phospholipids, *Biochem J*, 119, 481-488; and Macara, I. G. (1989) Elevated phosphocholine concentration in ras-transformed NIH 3T3 cells arises from increased choline kinase activity, not from phosphatidylcholine breakdown. *Mol Cell Biol*, 9, 325-328) suggesting that propargyl choline mimics well the properties of choline in cells.

Choline-containing phospholipids are synthesized in the endoplasmic reticulum (ER). From the ER these phospholipids need to reach other cellular membranes, such as the plasma membrane and the membranes of organelles such as mitochondria and the Golgi. FIG. 4 shows the distribution of propargyl choline-labeled phospholipids to cellular membranes. The ability of propargyl choline-labeled phospholipids to populate various cellular membranes known to contain choline phospholipids was examined. The plasma membrane, the Golgi, mitochondria and the ER were labeled by expression of specific red fluorescent protein (RFP) fusions, after which the cells were incubated with 100 microM propargyl choline overnight, fixed and stained with fluorescein-azide. As shown in FIG. 4A, the propargyl choline stain co-localizes with all four subcellular markers, demonstrating that propargyl choline-labeled phospholipids synthesized in the ER are subsequently distributed to other cellular membranes.

To obtain additional evidence that propargyl choline-labeled phospholipids reach the plasma membrane, a method to visualize the propargyl choline stain specifically on the cell surface was employed. Cells labeled with propargyl choline were fixed and then reacted simultaneously with both Alexa568-azide and biotin-azide. After removal of unincorporated azides, biotin attached to propargylcholine-labeled phospholipids was detected with Alexa488-streptavidin. Alexa568-azide penetrates the fixed cells to reveal both surface and intracellular phospholipids while the tetrameric Alexa488-streptavidin (having a molecular weight of 55 kDa) is only able to bind the biotin groups exposed on the cell surface. As shown in FIG. 4B, propargyl choline-labeled cells show strong surface labeling with biotin-azide and fluorescent streptavidin staining. In contrast, unlabeled cells evidenced very low background staining. This result demonstrates that propargylcholine-labeled phospholipids efficiently reach the outer leaflet of the plasma membrane.

Figure 5:
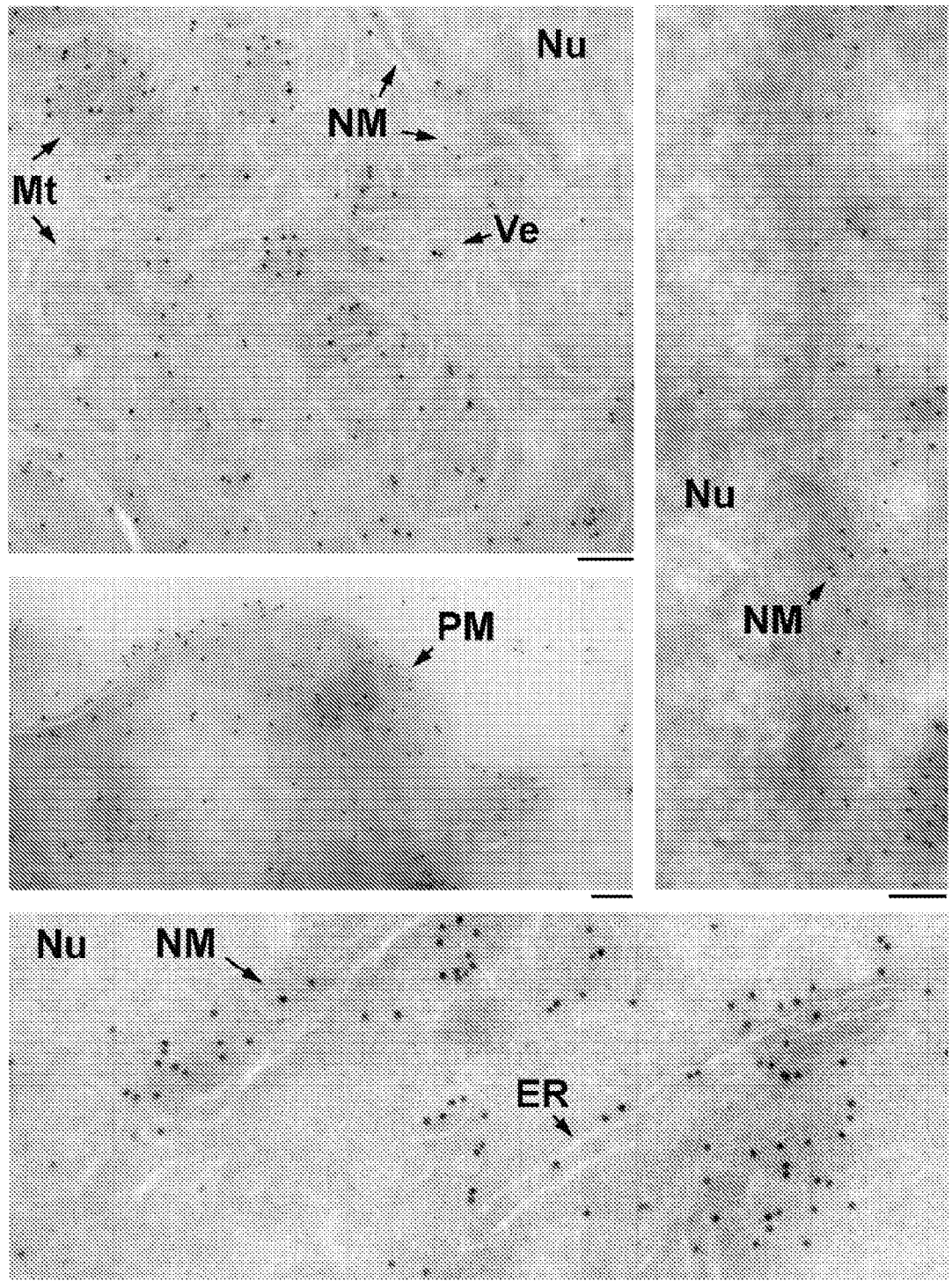
FIG. 5 is a series of images visualizing propargyl choline-labeled phospholipids by immuno-electron microscopy of cultured 293T cells labeled with 100 microM propargyl choline overnight, fixed, sectioned and stained with biotin-azide. The sections were then stained with anti-biotin antibodies and protein A-gold, counterstained with uranyl acetate and imaged by transmission electron microscopy. Arrows point to various structures: Mt, mitochondria; Nu, nucleus; ER, endoplasmic reticulum; PM, plasma membrane; NM, nuclear membrane; Ve, vesicle. The scale bar in all panels is 100 nm.

Phospholipids in cells or tissues labeled in accordance with the present compositions and methods can be imaged or visualized using any appropriate optical or electron microscopy technique. In one embodiment, immuno-electron microscopy was used to determine precisely what organelles contain propargylcholine-labeled phospholipids. Cultured cells incubated overnight with or without 100 microM propargyl choline were fixed, sectioned, frozen on an ultramicrotome and reacted with biotin-azide. Biotin was detected using anti-biotin antibodies and protein A-gold and the cell sections were negatively stained with uranyl acetate and imaged by transmission electron microscopy. As shown in the gallery of micrographs in FIG. 5, in propargylcholine-labeled cells large numbers of gold particles localize to mitochondria, the plasma membrane, the nuclear membrane, the endoplasmic reticulum and a large number of vesicles. Gold particles are largely absent from the nuclei of propargyl choline-labeled cells as well as from areas of cytoplasm devoid of membranous structures. In contrast, sections through unlabeled cells have little to no gold particles, demonstrating the specificity of the immunogold stain. These experiments further demonstrate that propargyl choline labels phospholipids in cellular membranes that are known to contain choline phospholipids. They also demonstrate a method for the direct visualization of choline phospholipids by electron microscopy in cells.

The compositions and methods of the present invention can be used to label and image phospholipids in whole animals, as demonstrated by the following experiment. One milligram of propargyl choline was injected intraperitoneally into a 3-week old mouse. Various organs were harvested and fixed 24 hours later, followed by fluorescent azide staining of cryostat sections. The results, shown in FIG. 6, indicate that propargyl choline shows very strong labeling of mouse tissues. In liver, the site of abundant phospholipids synthesis, all hepatocytes incorporate propargyl choline. Staining is also strong in intestine, kidney and spleen. Sections from an uninjected control mouse show very low background staining. The present method thus is suitable for visually assaying the synthesis, degradation and steady state levels of choline phospholipids in organs and tissues.

The cell biology of phospholipids remains obscure. It is not understood how phospholipid synthesis is regulated in cells, how these phospholipids spread from their place of synthesis to other locations in the cell, how they are transported between different cellular organelles, how they move between the leaflets of membrane bilayers (flip-flop) or how they are organized into membrane microdomains. The present invention provides an effective and robust method for metabolically labeling phospholipids, especially choline phospholipids, in living cells and tissues, which allows the biosynthetic pathway of these phospholipids to be followed by high-resolution microscopic imaging in cells.

The present method is based on the metabolic incorporation of a head group precursor analog bearing a terminal or internal alkyne group into phospholipids. The resulting alkyne-functional phospholipid molecules can be visualized with high sensitivity and spatial resolution in cells by reacting the terminal alkyne group with a labeled azide, and visualizing the resulting labeled phospholipids. The methods can be used in cultured cells or living animals to image phospholipid synthesis, turnover and subcellular localization. Utilizing a copper-free alkyne-azide reaction, such as described by Baskin et al. (Baskin et al., (2007) Copper-free click chemistry for dynamic in vivo imaging, *PNAS*, 104(43), 16793-16797) and Bertozzi et al. (Codelli et al., (2008) Second-Generation difluorinated cyclooctanes for copper-free click chemistry. *J Am Chem Soc*, 130, 11486-11493; and Stetten and Bertozzi, (2008) A hydrophilic azacyclooctane for Cu-free click chemistry, *Org. Letts*, 10(14), 3097-3099), to label the alkyne-bearing phospholipids obtained by the present methods enables dynamic in vivo imaging of phospholipids.

The phospholipid biosynthetic pathway has been implicated in malignancy (Kwee et al., (2007) Cancer imaging with fluorine-18-labeled choline derivatives, *Semin Nucl Med*, 37(6), 420-8). For example, it has been reported that phosphatidyl-choline tends to localize at higher levels in the ER and Golgi apparatus of drug-sensitive and multidrug resistant human breast carcinoma cells compared to normal non-cancerous breast cells (Villa et al., (2005) Choline and phosphatidylcholine fluorescent derivatives localization in carcinoma cells studied by laser scanning confocal fluorescence microscopy, *Eur J Cancer*, 41(10), 1453-9). The compositions and methods of the present invention can provide a powerful method for visualizing the levels of phosphatidyl choline (or other phospholipids) in tumor samples, or in tumors in vivo. The compositions and methods of the present invention also can be used in drug discovery to identify drug candidates that affect or inhibit cellular biosynthesis, turnover or distribution of phospholipids in cells and tissues. The compositions and methods of the present invention also can be used to screen existing drugs or drug candidates to determine whether these compounds adversely affect phospholipid biosynthesis, e.g., to detect a cytotoxic effect caused by the interference of these compounds with normal biosynthesis, turnover or distribution of phospholipids in cells and tissues.

The present invention further comprises assays and kits for determining in a patient the presence of a disorder in the phospholipid biosynthetic pathway, or characterized by abnormal concentrations or localization of phospholipids, for example. According to one aspect, a formatted assay can be used for determining such a disorder by visualizing the biosynthesis, distribution or localization of phospholipids of interest in the cells or tissue of a patient. The assays may be formulated into kits that include all or some of the materials needed to conduct the analysis, including reagents (alkynyl head group analogs, azide-detectable labels, etc.) and instructions.

In one aspect, the assay method of the invention comprises contacting living cells or a xenograft grown from a biological sample from a patient with an alkynyl head group analog, allowing the cells or xenograft to incorporate the analog, followed by staining the fixed cells or a xenograft tissue with an azide-detection agent, and visualizing the samples. Alternatively, the alkynyl head group analog can be administered to a living animal and allowed to incorporate into the tissue of the animal. A tissue sample from the animal then can be stained with the azide reagent as described above. Use of a copper-free azide staining reaction would permit visualization in vivo.

The present invention further comprises a kit containing reagents for visualizing the biosynthesis, distribution or localization of phospholipids in tissue samples or cells from patients suspected of having a disorder in the phospholipid biosynthetic pathway, or characterized by abnormal concentrations or localization of phospholipids. Such a kit comprises, at a minimum, an alkyl derivative of a phospholipid head group and an azide reagent bearing a detectable label. The kit optionally may contain additional reagents and/or instructions for carrying out the assay.

Definitions

All definitions, as defined and used herein, should be understood to control over dictionary definitions, definitions in documents incorporated by reference, and/or ordinary meanings of the defined terms.

The articles "a" and "an" are used herein to refer to one or to more than one (i.e., to at least one) of the grammatical object of the article.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The term "alkyl" means an aliphatic or cyclic hydrocarbon radical containing from 1 to 12 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 2-methylcyclopentyl, and 1-cyclohexylethyl.

The term "alkynyl" as used herein means a straight or branched chain hydrocarbon group containing from 2 to 10 carbon atoms and containing at least one carbon-carbon triple bond. Representative examples of alkynyl include, but are not limited to, acetylenyl, 1-propynyl, 2-propynyl, 3-butynyl, 2-pentynyl, and 1-butynyl.

The term "azido" as used herein means a —$N_3$ group. For example, an azido-alkyl group refers to an azido group bonded to an alkyl group and azidoethylbromide refers to an azido group bonded to an ethylbromide ($N_3CH_2CH_2Br$).

The term "leaving group" as used herein refers to any chemical fragment that is capable of being displaced by a nucleophile, such as the nitrogen atom of an amine. Acetate, sulfonate (e.g. triflate, mesylate, nonaflate and tosylate), phosphate, halogen (e.g. chloro, bromo or iodo), and nitro are examples of leaving groups.

Selected Methods and Compounds

One aspect of the invention relates to a method for forming an alkynyl-labeled or azido-labeled phospholipid in living cells comprising: contacting the living cells with a metabolic precursor having an alkynyl or azido moiety under conditions sufficient to allow the phospholipids in the cells to incorporate the precursor, thereby forming the alkynyl-labeled or azido-labeled phospholipid.

In certain embodiments, the present invention relates to any of the aforementioned methods, wherein the metabolic precursor is selected from the group consisting of choline, homocholine, inositol, ethanolamine and serine.

In certain embodiments, the present invention relates to any of the aforementioned methods, wherein the metabolic precursor has an alkynyl moiety; and an alkynyl-labeled phospholipid is formed.

In certain embodiments, the present invention relates to any of the aforementioned methods, wherein the alkynyl moiety comprises an alkynyl compound having two to five carbon atoms and a terminal alkynyl group.

In certain embodiments, the present invention relates to any of the aforementioned methods, wherein the alkynyl moiety comprises a cyclic alkynyl compound.

In certain embodiments, the present invention relates to any of the aforementioned methods, wherein the alkynyl compound is 2-propynyl (propargyl).

In certain embodiments, the present invention relates to any of the aforementioned methods, further comprising the step of reacting the alkynyl-labeled phospholipid with an azide compound having a detectable label.

In certain embodiments, the present invention relates to any of the aforementioned methods, wherein the metabolic precursor has an azido moiety; and an azido-labeled phospholipid is formed.

In certain embodiments, the present invention relates to any of the aforementioned methods, wherein the azido moiety comprises an azido compound having one to five carbon atoms and a terminal azido group.

In certain embodiments, the present invention relates to any of the aforementioned methods, wherein the azido compound is azidoethyl.

In certain embodiments, the present invention relates to any of the aforementioned methods, further comprising the step of reacting the azido-labeled phospholipid with an alkyne compound having a detectable label.

Another aspect of the invention relates to a method for visualizing phospholipids in living cells comprising: contacting the living cells with a precursor having an alkynyl or azido moiety under conditions sufficient to allow the phospholipids in the cells to incorporate the precursor, thereby forming an alkynyl-labeled or azido-labeled phospholipid; contacting the cells with a detectable label having an azide or alkyne group under conditions sufficient to allow the azide or alkyne group to react with the alkynyl or azido moiety, thereby forming phospholipids labeled with the detectable label; and visualizing the detectable label using optical or electron microscopy.

In certain embodiments, the present invention relates to any of the aforementioned methods, wherein the metabolic precursor is selected from the group consisting of choline, homocholine, inositol, ethanolamine and serine.

In certain embodiments, the present invention relates to any of the aforementioned methods, wherein the precursor has an alkynyl moiety; an alkynyl-labeled phospholipid is formed; and the cells are contacted with a detectable label having an azido group.

In certain embodiments, the present invention relates to any of the aforementioned methods, wherein the alkynyl moiety comprises an alkynyl compound having between two to five carbon atoms and a terminal alkynyl group.

In certain embodiments, the present invention relates to any of the aforementioned methods, wherein the alkynyl moiety comprises a cyclic alkynyl compound.

In certain embodiments, the present invention relates to any of the aforementioned methods, wherein the alkynyl compound is 2-propynyl (propargyl).

In certain embodiments, the present invention relates to any of the aforementioned methods, wherein the detectable label having an azide group comprises biotin azide, TMR-azide, fluorescein azide or Alexa568-azide.

In certain embodiments, the present invention relates to any of the aforementioned methods, wherein the precursor has an azido moiety; an azido-labeled phospholipid is formed; and the cells are contacted with a detectable label having an alkyne group.

In certain embodiments, the present invention relates to any of the aforementioned methods, wherein the azido moiety comprises an azido compound having one to five carbon atoms and a terminal azido group.

In certain embodiments, the present invention relates to any of the aforementioned methods, wherein the azido compound is azidoethyl.

In certain embodiments, the present invention relates to any of the aforementioned methods, wherein the detectable label having an alkenyl group comprises alkenyl-labeled bioton, alkyenyl-labeled TMR, alkenyl-labeled azide or alkenyl-labeled Alexa568.

Another aspect of the invention relates to a compound comprising an alkynyl derivative of choline, alkynyl derivative of homocholine, an alkynyl derivative of ethanolamine, and alkynyl derivative of inositol, or an alkynyl derivative of serine.

In certain embodiments, the present invention relates to any of the aforementioned compounds, wherein the alkynyl moiety is an alkyl-alkyne having 2 to 5 carbon atoms and a terminal alkynyl group.

In certain embodiments, the present invention relates to any of the aforementioned compounds, wherein the alkynyl moiety comprises a cyclic alkynyl compound.

In certain embodiments, the present invention relates to any of the aforementioned compounds, wherein the alkynyl moiety is propargyl.

Another aspect of the invention relates to a compound comprising propargyl-choline, propargyl-homocholine, propargyl-ethanolamine, propargyl-serine or propargyl-inositol.

Another aspect of the invention relates to a compound comprising phosphatidyl-alkynyl-choline, phosphatidyl-alkynyl-homocholine, phosphatidyl-alkynyl-ethanolamine, phosphatidyl-alkynyl-inositol or phosphatidyl-alkynyl-serine.

In certain embodiments, the present invention relates to any of the aforementioned compounds, wherein the alkynyl moiety is an alkyl-alkyne having 2 to 5 carbon atoms, and a terminal alkynyl group.

In certain embodiments, the present invention relates to any of the aforementioned compounds, wherein the alkynyl moiety comprises a cyclic alkynyl compound.

In certain embodiments, the present invention relates to any of the aforementioned compounds, wherein the alkynyl moiety is propargyl.

Another aspect of the invention relates to a compound comprising phosphatidyl-propargyl-choline, phosphatidyl-alkynyl-homocholine, phosphatidyl-propargyl-ethanolamine, phosphatidyl-propargyl-inositol and phosphatidyl-propargyl-serine.

Another aspect of the invention relates to a compound comprising an azide derivative of choline, an azide derivative of ethanolamine, and azide derivative of inositol, or an azide derivative of serine.

In certain embodiments, the present invention relates to any of the aforementioned compounds, wherein the azide moiety is an alkyl-azide having between 1 to 5 carbon atoms and a terminal azido group.

Another aspect of the invention relates to a compound comprising phosphatidyl-choline-$(CH_2)_x$-azide, phosphatidyl-homocholine-(CH$_2$)$_x$-azide, phosphatidyl-ethanolamine-(CH$_2$)$_x$-azide, phosphatidyl-inositol-(CH$_2$)$_x$-azide and phosphatidyl-serine-(CH$_2$)$_x$ azide, where x is 1 to 5.

Another aspect of the invention relates to a method for forming an alkynyl-functional or azido-functional phospholipid head group precursor comprising: contacting a phospholipid head group precursor with an alkynyl or azido moiety under conditions sufficient to allow the alkynyl or azido moiety to covalently attach to the head group precursor, thereby forming the alkynyl-functional or azido-functional phospholipid head group precursor.

In certain embodiments, the present invention relates to any of the aforementioned methods, wherein the head group precursor is selected from the group consisting of choline, homocholine, inositol, ethanolamine and serine.

In certain embodiments, the present invention relates to any of the aforementioned methods, wherein the phospholipid head group precursor is contacted with an alkynyl moiety; and an alkynyl-functional phospholipid head group precursor is formed.

In certain embodiments, the present invention relates to any of the aforementioned methods, wherein the alkynyl moiety comprises an alkynyl compound having two to five carbon atoms and a terminal alkynyl group.

In certain embodiments, the present invention relates to any of the aforementioned methods, wherein the alkynyl compound is 2-propynyl (propargyl).

In certain embodiments, the present invention relates to any of the aforementioned methods, wherein the alkynyl moiety comprises a cyclic alkynyl compound.

In certain embodiments, the present invention relates to any of the aforementioned methods, wherein the cyclic alkynyl compound is cyclooctyne.

In certain embodiments, the present invention relates to any of the aforementioned methods, wherein the phospholipid head group precursor is contacted with an azido moiety; and an azido-functional phospholipid head group precursor is formed.

In certain embodiments, the present invention relates to any of the aforementioned methods, wherein the azido moiety comprises an azido compound having one to five carbon atoms and a terminal azido group.

In certain embodiments, the present invention relates to any of the aforementioned methods, wherein the azido compound is azidoethyl.

EXEMPLIFICATION

The invention now being generally described, it will be more readily understood by reference to the following, which is included merely for purposes of illustration of certain aspects and embodiments of the present invention, and is not intended to limit the invention.

Example 1

Synthesis of Propargyl Choline

Propargyl-choline was synthesized by the following procedure: 4 grams of propargyl bromide (80% solution in toluene, 34 mmoles) were slowly added to 3 grams of dimethylethanolamine (34 mmoles) in 10 mL of dry THF, while stirring on ice. The mix was allowed to reach room temperature and stirring was continued overnight. The resulting white solid was filtered and washed extensively with cold THF (10 times, 20 mL), to afford pure propargyl-choline bromide (5.9 grams, 84% yield) as a white solid. Propargyl-choline: white crystals, molecular weight: 128.19, ES-API LC/MS: [M]$^+$ =128.1, $^1$H NMR (600 MHz, CD$_3$OD): 4.78 (1H, b), 4.49 (2H, d, J=2.4 Hz), 4.03 (2H, t, J=4.5 Hz), 3.64 (2H, m), 3.30 (6H, s), $^{13}$C NMR (600 MHz, CD$_3$OD): δ3.2 (CH, d, J=101.4 Hz), 72.7 (C, d, J=21.0 Hz), 66.4 (CH$_2$, t, J=60.3 Hz), 56.7 (CH$_2$, t, J=47.4 Hz), 56.5 (CH$_2$, t, J=45.9 Hz), 52.2 (C$_2$H$_6$, q, J=31.2 Hz), 49.05 (CD$_3$OD).

Example 2

Labeling of Cultured Cells with Propargyl-Choline and Detection by Fluorescence Microscopy NIH-3T3 cells were grown on glass coverslips in DMEM with 10% bovine calf serum. Cells were labeled in complete media with propargyl-choline bromide (added from a 1M stock in water), washed with PBS and fixed with 3.7% formaldehyde in PBS for 30 minutes. The fixed cells were reacted with 10-20 microM fluorescent azide (Alexa568-azide or fluorescein-azide) as described by Salic and Mitchison (Salic, A., and Mitchison, T J. (2008) A chemical method for fast and sensitive detection of DNA synthesis in vivo. *Proc Natl Acad Sci, USA* 105, 2415-2420), washed with TBS (3 times), 0.5 M NaCl (twice) and again TBS (3 times). See, also, International Patent Application Nos. PCT/US2006/042287 and PCT/US2006/041885, both of which are hereby incorporated by reference in their entireties.

After counterstaining with Hoechst, the cells were imaged by fluorescence microscopy and DIC. The propargyl-choline stain is very sensitive to treatments that extract phospholipids from cell membranes, both before and after the reaction with the azide. To obtain the best results, detergents and organic solvents preferably should be avoided when performing a propargyl-choline stain on cells or on tissue sections.

The red fluorescent protein fusions used to determine co-localization with the propargyl-choline stain were DsRed-Mito (for mitochondria, Clontech), mCherry-Sec61 (for endoplasmic reticulum), tdTomato-GalT (for the Golgi apparatus) and mCherry-CAAX (for the plasma membrane). Plasmids encoding these constructs were transiently transfected into cultured cells, followed by labeling the cells with 100 microM propargyl-choline overnight. The cells were fixed, stained with fluorescein-azide and imaged by fluorescence microscopy.

To reveal propargyl-choline labeling of phospholipids on the cell surface (FIG. 4B), Alexa568-azide (10 microM) and biotin-azide (40 microM) were mixed in the same staining reaction. After azide staining and washing, the cells were incubated with block solution (40 mg/mL BSA in TBS), and biotin on the cell surface was detected by staining with 2 microg/mL Alexa488-streptavidin (Molecular Probes) in block solution. The cells were washed with TBS, counterstained with Hoechst and imaged by fluorescence microscopy.

To test the effect of detergent on the propargyl-choline stain, propargyl-choline-labeled cells were washed with PBS, incubated with PBS+0.1% Triton-X100 for 5 minutes at room temperature followed by formaldehyde fixation. Control cells were incubated in parallel without detergent. To test the phospholipase sensitivity of the propargyl choline stain, cells labeled with 100 microM propargyl choline overnight were fixed with 3.7% formaldehyde in PBS, rinsed with TBS and incubated for 1 hr at 37° C. in TBS pH 7.5 with 1 mg/mL BSA, in the presence or absence of 0.02 unit/mL phospholipase C (PLC type XIV from *C. perfringens*, Sigma), with 10 mM CaCl$_2$ (required for PLC activity) or 10 mM EDTA (as an inactive PLC control). The cells were washed with TBS and then stained with Alexa568-azide as described above.

Example 3

Detection of Propargyl-Choline-Labeled Phospholipids In Vivo in Mice

Fifty microliters of a 1M solution of propargyl-choline in PBS were injected intraperitoneally into a 3-week old mouse. Tissues were removed 24 hours later and fixed in formalin. An uninjected mouse was used as control. The tissues were embedded in OCT medium (Tissue-Tek) and sectioned on a cryostat, followed by staining with 40 microM tetramethyl-rhodamine (TMR)-azide and Hoechst, as described for cultured cells in Example 2. The sections were washed extensively with 0.5M NaCl and with TBS, to remove unreacted azide. Extensive washes were required because of the thickness of the cryostat sections.

Figure 6:
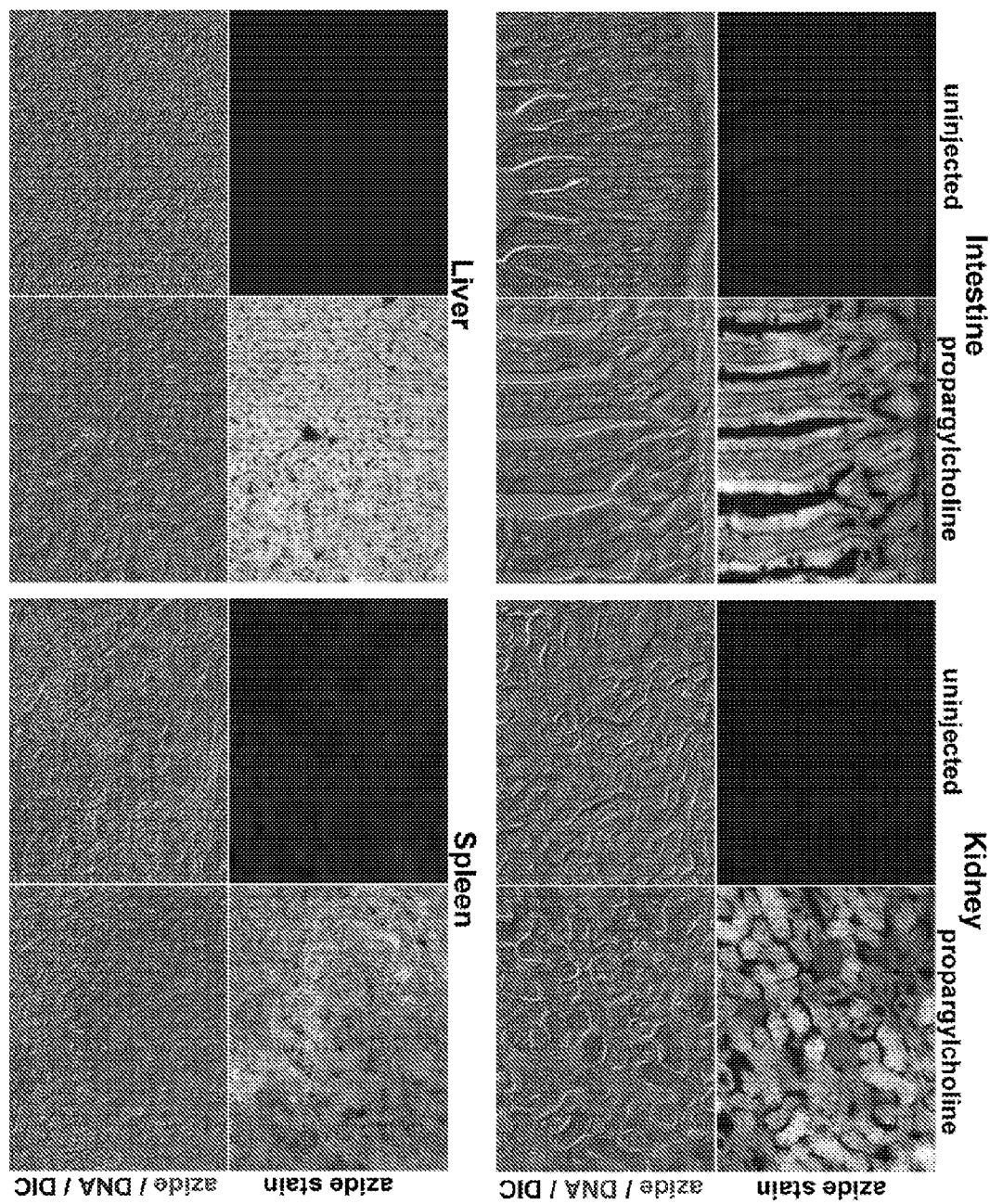
FIG. 6 is a series of images showing the synthesis of choline-containing phospholipids in vivo. Cryostat sections of various organs (small intestine, liver, spleen and kidney) from a propargyl choline-injected mouse and from an uninjected control mouse were stained in parallel with TMR-azide and show strong propargyl-choline incorporation in all tissues.

As shown in FIG. 6, propargyl-choline shows very strong labeling of mouse tissues. In liver, the site of abundant phospholipids synthesis, all hepatocytes incorporate propargyl-choline. Staining is also strong in intestine, kidney and spleen. Sections from an uninjected control mouse show very low background staining. These results demonstrate that the present method is suitable for visually assaying the synthesis of propargyl-choline phospholipids in living organs and tissues Example 4

Detection of Propargyl-Choline-Labeled Phospholipids by Electron Microscopy

Cultured 293T cells were grown overnight in DMEM supplemented with 10% fetal bovine serum, with or without 100 microM propargyl-choline. The cells were washed with PBS, detached from the dish in PBS+0.5 mM EDTA, pelleted and fixed in 100 mM Na phosphate pH 7.4, 4% formaldehyde (EM Sciences), 0.1% glutaraldehyde (EM Sciences), as described by Griffiths (Griffiths, G. (1993) Fine structure immunocytochemistry. Springer Verlag). Fixed cell pellets were infiltrated with PBS+2.3M sucrose, frozen in liquid nitrogen and sectioned on an ultramicrotome at −120 C. The 80-100 nm sections were laid on formvar/carbon-coated copper grids for electron microscopy. The grids were stained with biotin-azide as described above for fluorescence microscopy. Biotin was detected using a rabbit anti-biotin antibody (Rockland Immunochemicals), followed by protein A-gold (10 nm colloidal gold, Sigma). The grids were counterstained and embedded by incubation with 0.3% uranyl acetate in 2% methyl-cellulose as described by Griffiths (Griffiths, G. (1993) Fine structure immunocytochemistry. Springer Verlag). The cells were imaged on a Tecnai G2 Spirit BioTWIN transmission electron microscope equipped with an AMT 2 k CCD camera.

Example 5

Lipid Isolation and Analysis by LC/MS

Total lipids from NIH-3T3 cells labeled overnight with 500 microM propargyl choline and from untreated controls were isolated by methanol-chloroform extraction as described by Stith (Petcoff, D. W., et al. (2008) Lipid levels in sperm, eggs, and during fertilization in *Xenopus laevis. J Lipid Res*, 49, 2365-2378). The solvent was removed under reduced pressure and equal amounts of the total lipids were separated on an Agilent 1200 HPLC equipped with an evaporative light scattering detector (ELSD), using a 9.5×250 mm, 5 micron silica gel column, at a flow rate of 3 mLs/min, as previously described (Petcoff, D. W., et al. (2008) Lipid levels in sperm, eggs, and during fertilization in *Xenopus laevis. J Lipid Res*, 49, 2365-2378). Lipid standards for 1,2-dioleoyl phosphatidylethanolamine (PE), bovine liver phosphatidylinositol (PI), 1,2-dioleoyl phosphatidylserine (PS), 1,2-dioleoyl phosphatidylcholine (PC), and chicken egg sphingomyelin (SM) were from Avanti Polar Lipids. The results are shown in FIG. 2. Under the above conditions, the retention times were: 21.7 min for PE, 25.3 min for PI, 34.1 min for PS, 39.4 min for PC, and 43.5 min for SM. Phosphatidylcholine labeled with propargyl choline was detected as a broad peak with a retention time of 33.0 min.

To identify propargyl choline incorporated into phospholipids, HPLC fractions were collected and evaporated under reduced pressure. The dried lipid fractions were resuspended in water by sonication, adjusted to 60 mM sodium phosphate pH 7.4, 10 mM $CaCl_2$ and 10 units/mL phospholipase D (cabbage PLD, Sigma-Aldrich, P8398), and incubated at 37° C. for 1 hr to release the phospholipid head groups. The samples were centrifuged at 10,000 rpm for 5 min and the supernatants were analyzed by LC/MS for the presence of choline and propargyl choline ions, on an Agilent 6130 Quadrupole LC/MS system, using a 4.6×100 mm Luna C-18 column.

Example 6

Quantitative Analysis of Propargyl Choline Incorporation into Phospholipids

Total lipids were isolated from 293T cells labeled for 24 hours with either 250 microM or 500 microM propargyl choline in complete media (DMEM+10% fetal calf serum). The total lipids were treated with PLD, followed by LC/MS analysis as above. Mass-to-charge ratios of 104 (choline) and 128 (propargyl choline) were extracted from the mass spectra and their peaks integrated using Agilent Chemstation software. The peak areas were converted to nmols of choline and propargyl choline using linear calibration curves obtained from standards of pure choline and propargyl choline. These values were used to calculate the molar ratio between choline and propargyl choline in the total lipid samples.

In the above Examples, unless otherwise noted, all chemicals were obtained from Aldrich and were used without further purification. TMR-azide, fluorescein-azide and Alexa568-azide were described before by Salic and Mitchison (Salic, A., and Mitchison, T J. (2008) A chemical method for fast and sensitive detection of DNA synthesis in vivo. *Proc Natl Acad Sci, USA* 105, 2415-2420) and Jao and Salic (Jao, C. Y., and Salic, A. (2008) Exploring RNA transcription and turnover in vivo by using click chemistry. *Proc Natl Acad Sci USA* 105, 15779-15784). See, also, International Patent Application Nos. PCT/US2006/042287 and PCT/US2006/041885, both of which are hereby incorporated by reference in their entireties. Biotin azide was synthesized by reacting biotin-succinimidyl ester (Molecular Probes) with O-(2-aminoethyl)-O'-(2-azidoethyl)-pentaethylene glycol (Fluka) in dry DMSO according to the manufacturer's instructions.

Example 7

Detecting Azidophosphatidylcholines

Figure 9:
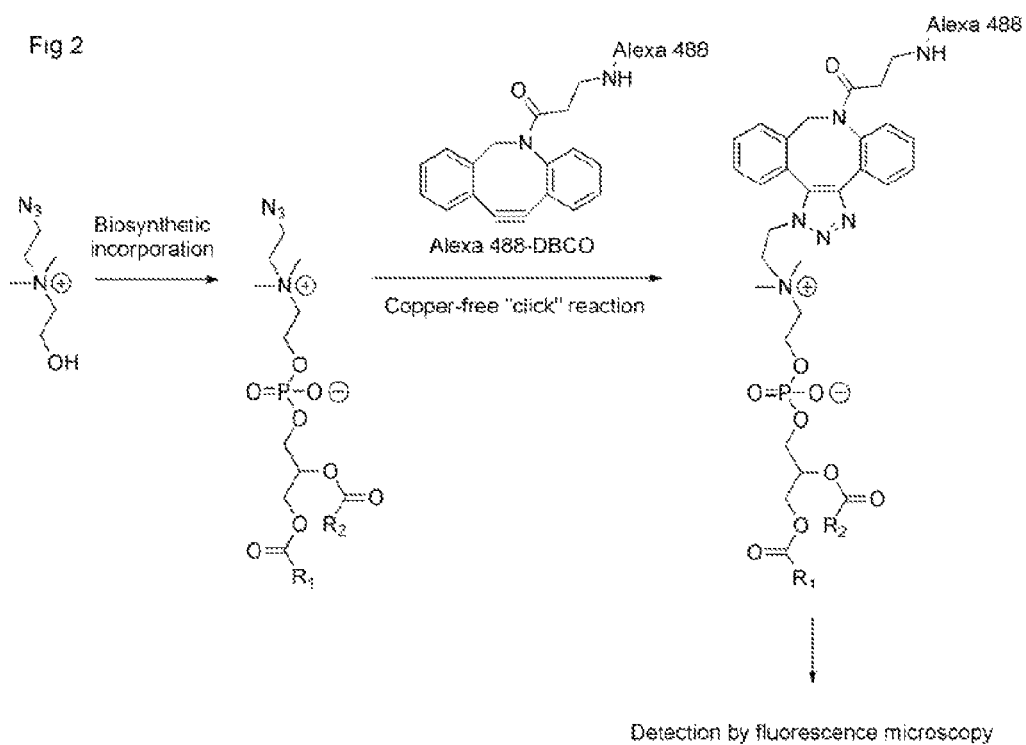
FIG. 9 depicts results of using a copper-free "click" reaction to visualize cells metabolically labeled with an azidocholine analogue (in this case, azidoethyl-choline).
Figure 10:
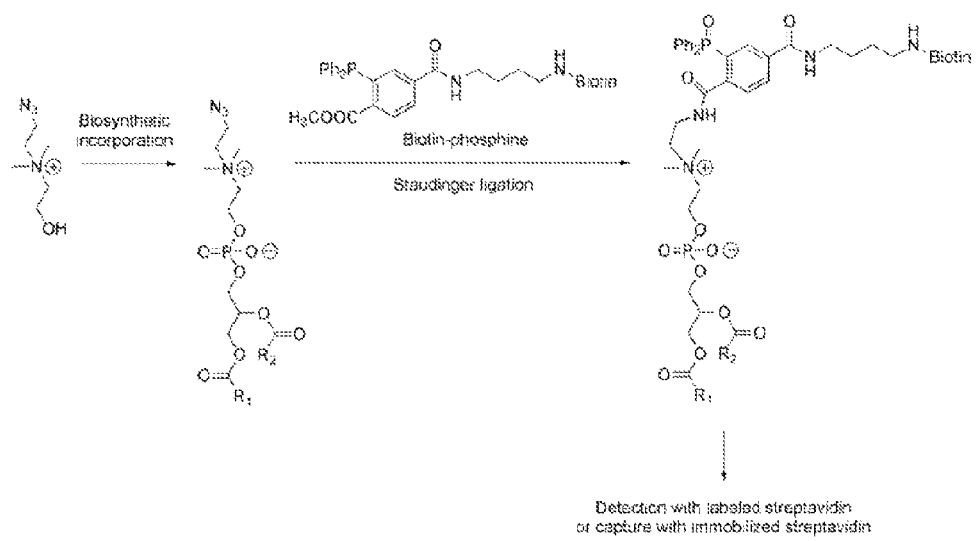
FIG. 10 depicts results of using the Staudinger ligation to detect cellular phospholipids metabolically labeled with an azido-choline analogue (in this case, azidoethyl-choline).

After incorporation into phospholipids, azidophosphatidylcholine molecules can be detected by specifically reacting them with a fluorescent conjugate of dibenzo-cyclooctyne (DBCO), in a strain-promoted azide-alkyne cycloaddition reaction, also known as the copper-free "click" reaction (FIG. 9). In addition, azidophosphatidylcholine molecules can be reacted with a biotin-phosphine, followed by the detection of the biotinylated phospholipid species using labeled streptavidin (FIG. 10).

Example 8

Detecting Phospholipids in Cells

Figure 11:
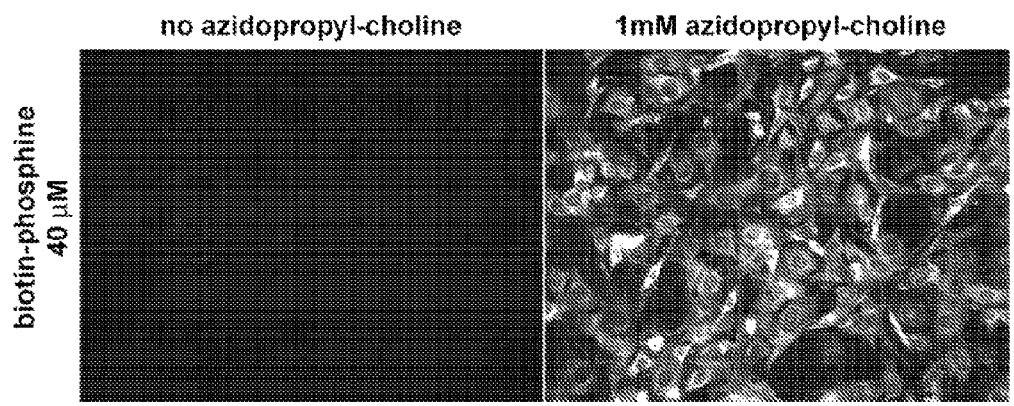
FIG. 11 depicts phospholipids in cells labeled with azidopropyl-choline.

Cultured NIH-3T3 cells on coverslips were incubated overnight in complete media (DMEM with 10% bovine calf serum) in the absence or presence of 1 mM azidopropyl-choline. The cells were then washed with PBS, fixed with 3.7% formaldehyde in PBS, washed with TBS and then reacted with 40 microM biotin-phosphine in TBS supplemented with 1 mM DTT, for 3 hours at room temperature. The cells were then washed successively with TBS, 0.5 M NaCl, and TBS. Non-specific binding sites were blocked by incubation with blocking buffer (4% bovine serum albumin in TBS), followed by staining with Alexa488-streptavidin (1 microg/mL in blocking buffer). The cells were then washed with TBS (at least 4 washes, at 5 minutes each), mounted and imaged by fluorescence microscopy. Results are shown in FIG. 11.

Example 9

Detecting Subcellular Distribution of Azidoethylcholine-Labeled Phospholipids

Figure 12:
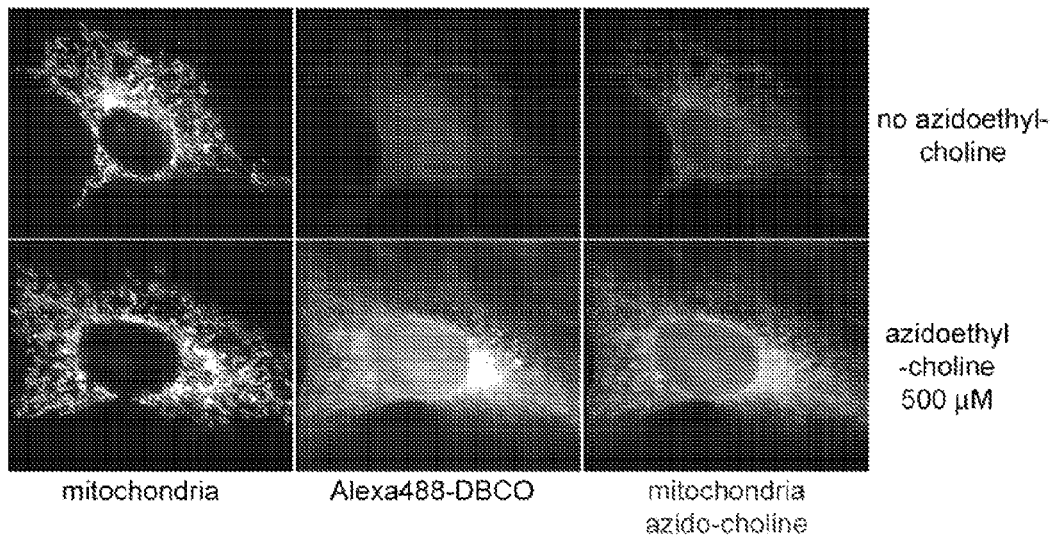
FIG. 12 depicts the subcellular distribution of azidoethyl-choline-labeled phospholipids.

Cultured NIH-3T3 cells were transiently transfected with the plasmid pDsRed-Mito (Clontech), which labels mitochondria red. The cells were then incubated overnight in complete media, in the absence or presence of 500 microM azidoethyl-choline. The cells were washed with PBS, fixed with 3.7% formaldehyde in PBS, washed with TBS and then reacted with 20 microM Alexa488-DBCO in TBS, for 30 minutes at room temperature. Unreacted Alexa488-DBCO was removed by washing successively with TBS, 0.5 M NaCl, and TBS. The cells were then imaged by fluorescence microscopy. Note that azido-choline labeled phospholipids localize to several populations of cellular membranes, including the mitochondrial membrane. Results are shown in FIG. 12.

Example 10

Figure 13:
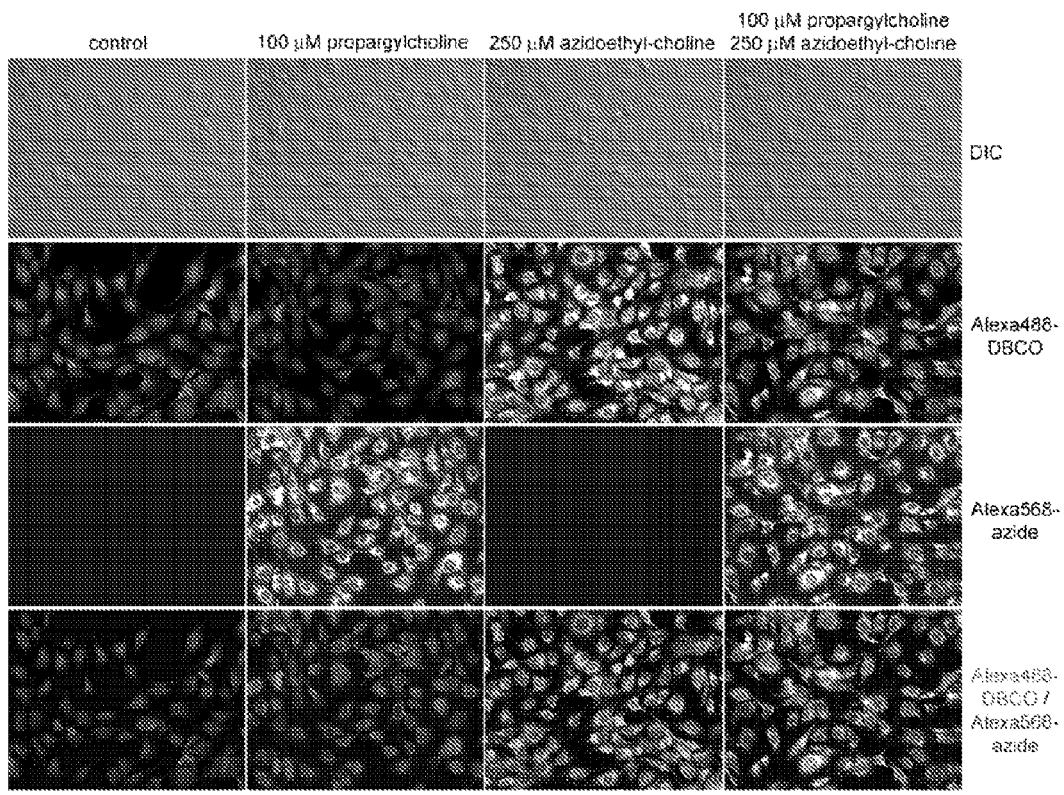
FIG. 13 depicts simultaneous detection of phospholipids in cells labeled with propargylcholine and azidoethyl-choline. Top row: DIC images of the cells; second row: azidoethyl-choline-labeled phospholipids stained with Alexa488-DBCO; third row: propargycholine-labeled phospholipids stained with Alexa568-azide; bottom row: overlay of the red (Alexa568) and green (Alexa488) images (color not shown). Co-localization of phospholipids molecules labeled with either propargylcholine or azidoethylcholine is observed.

Simultaneous Detection of Phospholipids in Cells Labeled with Propargyl-Choline and Azidoethyl-Choline Cultured NIH-3T3 cells were incubated overnight in complete media, in media with 100 microM propargylcholine, in media with 250 microM azidoethyl-choline, or in media with both 100 microM propargylcholine and 250 microM azidoethyl-choline. The cells were washed with PBS, fixed with 3.7% formaldehyde in PBS, washed with TBS and then reacted with 20 microM Alexa488-DBCO in TBS, for 30 minutes at room temperature. After removing of unincorporated Alexa488-DBCO, propargylcholine-labeled phospholipids were detected by copper-catalyzed "click" reaction (incubation with 10 microM Alexa568-azide in 100 mM Tris, 1 mM CuSO4, 100 mM ascorbate, pH 7, for 30 minutes at room temperature). The cells were then washed with TBS several times and imaged by fluorescence microscopy. Results are shown in FIG. 13.

INCORPORATION BY REFERENCE

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

EQUIVALENTS

The invention has been described broadly and generically herein. Those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention. Further, each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

What is claimed is:

1. A method for forming an alkynyl-labeled or azido-labeled phospholipid in living cells comprising:
   contacting the living cells with a compound under conditions sufficient to allow the phospholipids in the cells to incorporate the compound,
   wherein the compound is selected from the group consisting of alkynyl-functionalized choline, azido-functionalized choline, alkynyl-functionalized homocholine, azido-functionalized homocholine, alkynyl-functionalized inositol, azido-functionalized inositol, alkynyl-functionalized ethanolamine, azido-functionalized ethanolamine, alkynyl-functionalized serine, and azido-functionalized serine, thereby forming the alkynyl-labeled or azido-labeled phospholipid.

2. The method of claim 1, wherein the compound comprises two to five carbon atoms and a terminal alkynyl group.

3. The method of claim 1, wherein the compound comprises a cyclic compound.

4. The method of claim 1, wherein the compound comprises 2-propynyl.

5. The method of claim 1, wherein the compound has an azido moiety; and an azido-labeled phospholipid is formed.

6. The method of claim 5, wherein the compound comprises one to five carbon atoms and a terminal azido group.

7. The method of claim 5, wherein the compound comprises azidoethyl.

8. The method of claim 1, further comprising the step of reacting the alkynyl-labeled phospholipid with an azide compound having a detectable label; or reacting the azido-labeled phospholipid with an alkyne compound having a detectable label, wherein the detectable label is optically or electronically detectable.

9. A method for visualizing phospholipids in living cells comprising:
contacting the living cells with a compound selected from the group consisting of alkynyl-functionalized choline, azido-functionalized choline, alkynyl-functionalized homocholine, azido-functionalized homocholine, alkynyl-functionalized inositol, azido-functionalized inositol, alkynyl-functionalized ethanolamine, azido-functionalized ethanolamine, alkynyl-functionalized serine, and azido-functionalized serine under conditions sufficient to allow the phospholipids in the cells to incorporate the compound, thereby forming an alkynyl-labeled or azido-labeled phospholipid;
contacting the cells with a detectable label having an azide or alkyne group under conditions sufficient to allow the azide or alkyne group to react with the compound, wherein the detectable label is optically or electronically detectable, thereby forming phospholipids labeled with the detectable label; and
visualizing the detectable label using optical or electron microscopy,
wherein when the compound has an alkynyl moiety, the detectable label has an azide group; and when the compound has an azido moiety, the detectable label has an alkyne group.

10. The method of claim 9, wherein the compound comprises two to five carbon atoms and a terminal alkynyl group.

11. The method of claim 9, wherein the compound has an alkynyl moiety; and the compound comprises a cyclic compound.

12. The method of claim 9, wherein the compound comprises 2-propynyl.

13. The method of claim 9, wherein the detectable label is biotin azide, TMR-azide, fluorescein azide, or Alexa568-azide.

14. The method of claim 9, wherein the compound comprises one to five carbon atoms and a terminal azido group.

15. The method of claim 9, wherein the compound comprises azidoethyl.

16. The method of claim 9, wherein the detectable label is alkynyl-labeled biotin, alkynyl-labeled TMR, alkynyl-labeled azide, or alkynyl-labeled Alexa568.

17. The method of claim 1, wherein the compound is selected from the group consisting of:

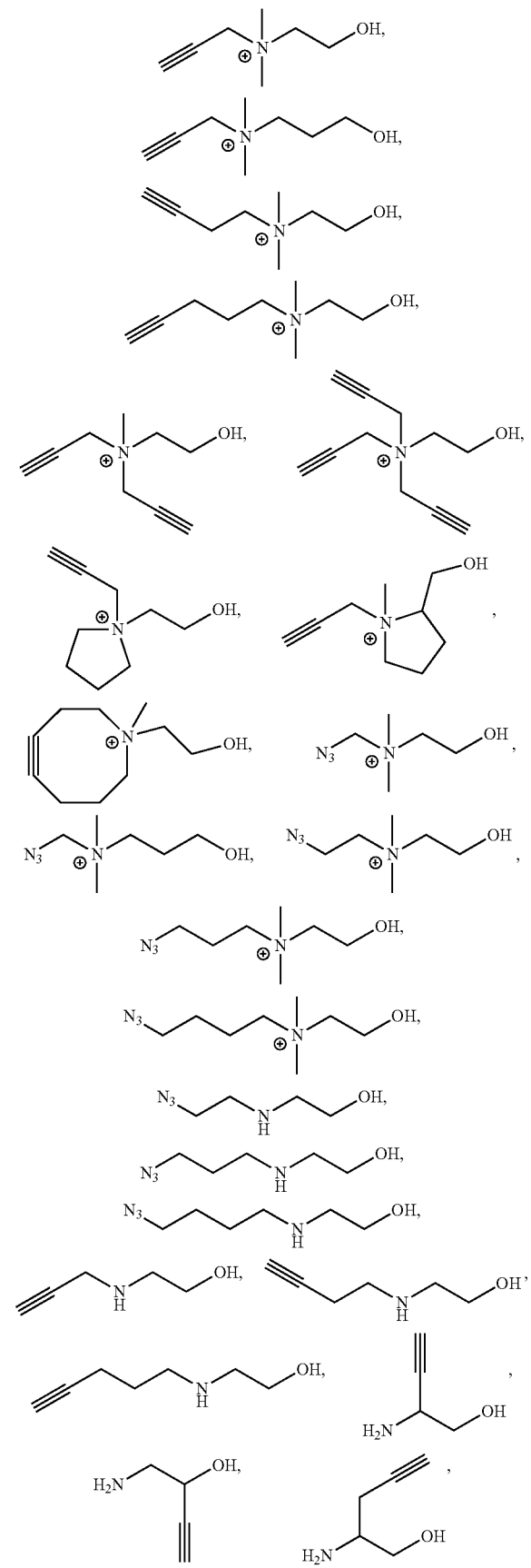

-continued
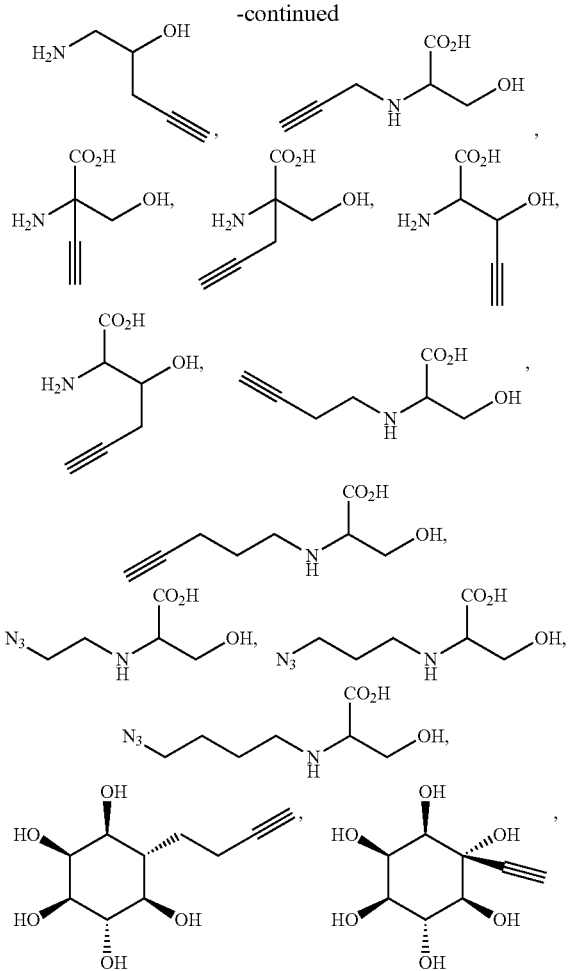
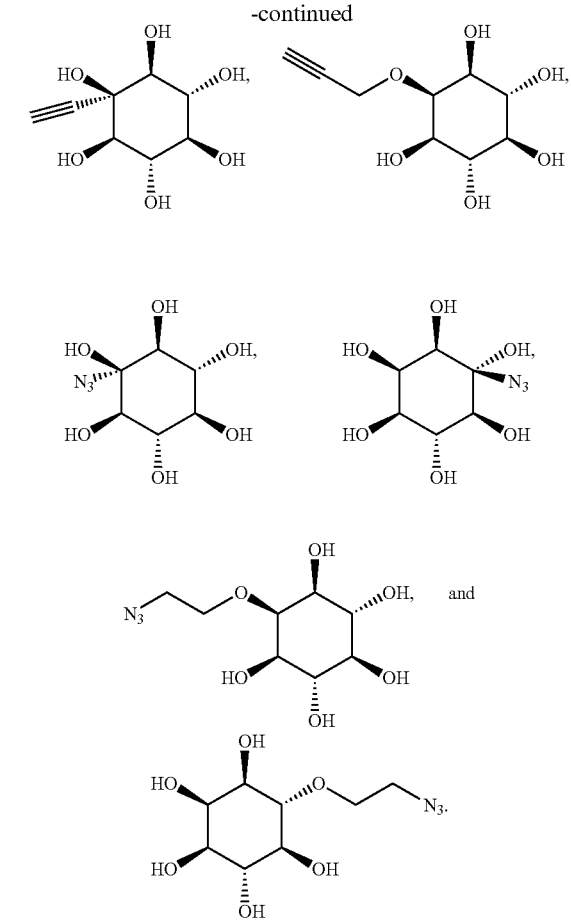
* * * * *